US009217173B2

(12) United States Patent
Engel et al.

(10) Patent No.: US 9,217,173 B2
(45) Date of Patent: Dec. 22, 2015

(54) METHOD OF POLYADENYLATION AND CDNA SYNTHESIS IN A SINGLE REACTION

(75) Inventors: Holger Engel, Hilden (DE); Subrahmanyam Yerramilli, Clarksville, MD (US); Martin Kreutz, Germantown, MD (US); Dirk Loeffert, Duesseldorf (DE); Christian Korfhage, Hilden (DE)

(73) Assignee: QIAGEN GMBH, Hilden (DE)

( * ) Notice: Subject to any disclaimer, the term of this patent is extended or adjusted under 35 U.S.C. 154(b) by 1694 days.

(21) Appl. No.: 12/377,457

(22) PCT Filed: Aug. 13, 2007

(86) PCT No.: PCT/EP2007/058369
§ 371 (c)(1),
(2), (4) Date: Nov. 21, 2011

(87) PCT Pub. No.: WO2008/020008
PCT Pub. Date: Feb. 21, 2008

(65) Prior Publication Data

US 2012/0202198 A1 Aug. 9, 2012

(30) Foreign Application Priority Data

Aug. 14, 2006 (DE) ........................ 10 2006 038 113

(51) Int. Cl.
*C12P 19/34* (2006.01)
*C12Q 1/68* (2006.01)

(52) U.S. Cl.
CPC .................................. *C12Q 1/6806* (2013.01)

(58) Field of Classification Search
USPC ...................................... 435/6.12, 91.1, 91.2
See application file for complete search history.

(56) References Cited

U.S. PATENT DOCUMENTS 8,314,220 B2 * 11/2012 Mullinax et al. ............ 536/22.1
2003/0113875 A1 6/2003 Gemen (Continued)

FOREIGN PATENT DOCUMENTS

CN 1763223 A 4/2006
JP 2002-505087 2/2002

(Continued)

OTHER PUBLICATIONS

Ambros, Victor, "The Functions of Animal MicroRNAs," Nature, vol. 431, pp. 350-355, Sep. 16, 2004.

(Continued)

*Primary Examiner* — Kenneth Horlick
(74) *Attorney, Agent, or Firm* — Fanelli Haag PLLC

(57) ABSTRACT

This invention relates to a process for synthesis of a cDNA in a sample, in an enzymatic reaction, wherein the process comprises the steps: simultaneous preparation of a first enzyme with polyadenylation activity, a second enzyme with reverse transcriptase activity, a buffer, at least one ribonucleotide, at least one deoxyribonucleotide, an anchor oligonucleotide; addition of a sample that comprises a ribonucleic acid; and incubation of the agents of the previous steps in one or more temperature steps, which are selected such that the first enzyme and the second enzyme show activity. The invention further relates to a reaction mixture that comprises a first enzyme with polyadenylation activity, a second enzyme with reverse transcriptase activity, optionally a buffer, optionally at least one ribonucleotide, optionally at least one deoxyribonucleotide, and optionally an anchor oligonucleotide. Moreover, the invention relates to a kit that comprises a corresponding reaction mixture.

20 Claims, 23 Drawing Sheets

RNA
Poly A Polymerase
rATP
Poly A Reaction
RNA + Poly A Tail
Purification
Reverse Transcription
dNTPs
Reverse Transcriptase
Oligo dT Tail Primer
Uni GAP dt
First Strand of cDNA
Tail
Tail-Specific Backward Primer
PCR
cDNA-Specific Forward Primer

(56) References Cited

U.S. PATENT DOCUMENTS

2005/0196782 A1* 9/2005 Kiefer et al. ...................... 435/6
2011/0124050 A1* 5/2011 Engel et al. .................. 435/91.2

FOREIGN PATENT DOCUMENTS

| | | |
|---|---|---|
| JP | 2006-504440 | 2/2006 |
| WO | WO 99/43850 | 9/1999 |
| WO | WO 2004/044239 | 5/2004 |
| WO | WO 2004/044239 A1 | 5/2004 |
| WO | WO 2005/064019 A2 | 7/2005 |

OTHER PUBLICATIONS

Ambros, Victor, "MicroRNAs: Tiny Regulators with Great Potential," Cell, vol. 107, pp. 823-826, Dec. 28, 2001.

Balakin, Andrey G., et al., "The RNA World of the Nucleolus: Two Major Families of Small RNAs Defined by Different Box Elements with Related Functions," Cell, vol. 86, pp. 823-834, Sep. 6, 1996.

Botero, Lina M., et al., "Poly(A) Polymerase Modification and Reverse Transcriptase PCR Amplification of Environment RNA," Applied and Environmental Microbiology, vol. 7, No. 3, pp. 1267-1275, Mar. 2005.

Chen, Chun-Long, et el., "The High Diversity of snoRNAs in Plants: Identification and Comparative Study of 120 snoRNA Genes from *Oryza sativa,*" Nucleic Acids Research, vol. 31, No. 10, pp. 2601-2613, 2003.

Fu, Hanjiang, et al., "Identification of Human Fetal Liver miRNAs by a Novel Method," FEBS Letters, vol. 579, pp. 3849-3854, 2005.

Landegren, Ulf, et al., "A Ligase-Mediated Gene Detection Technique," Science, vol. 241, pp. 1077-1080, Aug. 26, 1988.

Lee, Yoontae, et al., "The Nuclear RNase III Drosha Initiates MicroRNA Processing," Nature, vol. 425, pp. 415-419, Sep. 25, 2003.

Lee, Yoontae, et al., "MicroRNA Maturation: Stepwise Processing and Subcellular Localization," The EMBO Journal, vol. 21, No. 17, pp. 4663-4670, 2002.

Liu, Dongyu, et al., "Rolling Circle DNA Synthesis: Small Circular Oligonucleotides as Efficient Templates for DNA Polymerases," J Am Chem Soc, vol. 118, No. 7, pp. 1587-1594, 1996.

Martin, G., and W. Keller, "Tailing and 3'-end Labeling of RNA with Yeast Poly(A) Polymerase and Various Nucleotides," RNA, vol. 4, pp. 226-230, 1998.

Maxwell, E.S., and M. J. Fournier, "The Small Nucleolar RNAs," Ann Rev Biochem, vol. 35, pp. 897-934, 1995.

Olsen, Gary J., et al., "Microbial Ecology and Evolution: A Ribosomal RNA Approach," Ann Rev Microbiol, vol. 40, pp. 337-365, 1986.

Sano, Hiroshi, and Günter Feix, "Terminal Riboadenylate Transferase from *Escherichia coli,*" Eur J Biochem, vol. 71, pp. 577-583, 1976.

Shi, Rui, and Vincent L. Chiang, "Facile Means for Quantifying MicroRNA Expression by Real-Time PCR," BioTechniques, vol. 39, No. 4, pp. 519-524, 2005.

Walker, G. Terrance, et al., "Strand Displacement Amplification—an Isothermal, in vitro DNA Amplification Technique," Nucleic Acids Research, vol. 20, No. 7, pp. 1691-1696, 1992.

Wang, Jia-Fu, et al., "Identification of 20 MicroRNAs from *Oryza sativa,*" Nucleic Acids Research, vol. 32, No. 5, pp. 1668-1695, 2004.

Wiedmann, M., et al., "Ligase Chain Reaction (LCR)—Overview and Applications," Genome Research, vol. 3, pp. S51-S64, 1994.

Lao, et al., "Multiplexing RT-PCR for the detection of multiple miRNA species in small samples" Biochemical and Biophysical Research Communications, 343, (2006), 85-89.

Shi, et al., "Facile means for quantifying microRNA expression by real-time PCR" BioTechniques, 39:519-525, Oct. 2005.

Japanese Office Action, Application No. 2009-524183, dated Nov. 20, 2012, 4 pages.

International Search Report of PCT/EP2007/058369 (Dec. 12, 2007).

A. Hell et al., "Synthesis of DNA s Complementary to Human Ribosomal RNAs Polyadenylated in Vitro", Biochemica et Biophysica Acta, vol. 442 (1976) pp. 37-49.

J.H. Ko et al., "RNA-Conjugated Template-Switching RT-PCR Method for Generating an *Escherichia coli* cDNA Library for Small RNAs", Journal of Microbiological Methods, vol. 64 (2006) pp. 297-304.

* cited by examiner

| | a | b |
|---|---|---|
| 1) PAP Buffer | 25.50 | No Ct |
| 2) RT Buffer | 17.32 | No Ct |
| 3) Mixture of PAP RT Buffer | 30.28 | No Ct |
| 4) Two-stage Process | 25.64 | No Ct |

| | | PAP Puffer | RT Puffer | Standard RT |
|---|---|---|---|---|
| Reaction: 1, 4, 7 RNA, 2.5 ng + mleu7a | a) | 22.62 | 19.69 | No Ct |
| | b) RT Reaction Doubled | 24.30 | 19.76 | No Ct |
| Reaction: 2, 5, 8 RNA 2.5 ng | a) | 34.69 | 31.41 | No Ct |
| | b) RT Reaction Doubled | 34.20 | 32.77 | No Ct |
| Reaction 3, 6 H20 in PAP/RT | a) | No Ct | No Ct | |
| | b) RT Reaction Doubled | No Ct | No Ct | |

| | 1) β-Actin 3' Primer | 2.) leu7short | 3.) miR24 | 4.) miR15a | 5.) miR16 |
|---|---|---|---|---|---|
| b) PAP + RT | 23.16 | 25.30 | 28.47 | 25.90 | 23.83 |
| e) Standard RT | 22.75 | No CT | 30.95 | 39.81 | 38.78 |

| HumUni + | 1) β-Actin 3' Primer | 2.) leu7short | 3.) miR24 | 4.) miR15a | 5.) miR16 |
|---|---|---|---|---|---|
| b) $H_2O$ PAP + RT | No Ct | | | | |
| b) $H_2O$ Standard RT | | | | | |
| $H_2O$ in PCR | | | | | |

| | 6.) Hum Uni | 7.) leu7short | 8.) miR24 | 9.) miR15a | 10.) miR16 |
|---|---|---|---|---|---|
| a) 293 PAP + RT | No Ct | | | | |
| b) $H_2O$ PAP + RT | | | | | |
| c) 293 Standard RT | | | | | |
| d) $H_2O$ Standard RT | | | | | |
| H 0 in PCR | | | | | |

PAP + RT Reaction

| 2x10^8 Copies mleu7a + Corn RNA 5ng | 1.) 1 Hour of Incubation Time | | 2.) 15 min of Incubation Time | |
|---|---|---|---|---|
| | a) 2 U PAP Enzyme | b) 0.5 U PAP Enzyme | a) 2 U PAP Enzyme | b) 0.5 U PAP Enzyme |
| | 21.14 | 22.70 | 22.06 | 24.82 |

| | Reaction | 10x Buffer RT (Qiagen) | Reaction | Buffer Appropriate for the Enzyme |
|---|---|---|---|---|
| AMV Reverse Transcriptase 24 U | 1.) | 19.95 | 6.) | 20.23 |
| SuperScript III Reverse Transcriptase 10 U | 2.) | 16.78 | 7.) | 15.80 |
| HIV Reverse Transcriptase 1 U | 3.) | 18.55 | 8.) | 18.88 |
| M-MuLV Reverse Transcriptase 10 U | 4.) | 17.28 | 9.) | 14.86 |
| Sensiscript Reverse Transcriptase | 5.) | 20.75 | | |

| Synthetic miRNA | | |
|---|---|---|
| SEQ ID NO. 1 | mleu7a RNA | 5'-UGA GGU AGU AGG UUG UAU AGU U-3' |
| RT (Tail) Primer | | |
| SEQ ID NO. 2 | Uni GAP dT | 5'-TGG ACC GAG ACG ACG ACG ACA GAC CAA GCT TCC CGT TCT CAG CCT TTT TTT TTT TTT TTT TTT TTV VN-3' |
| PCP Primer | | |
| SEQ ID NO. 3 | Hum Uni | 5'-AAC GAG ACG ACG ACA GAC-3' |
| SEQ ID NO. 4 | Let 7short | 5'-GAG GTA GTA GGT TGT ATA G-3' |
| SEQ ID NO. 5 | hsa-miR-24 | 5'-TGG CTC AGT TCA GCA GCA GGA-3' |
| SEQ ID NO. 6 | hsa-miR-15a | 5'-TAG CAG CAC ATA ATG GTT T-3' |
| SEQ ID NO. 7 | hsa-miR-16 | 5'-TAG CAG CAC GTA AAT ATT G-3' |
| SEQ ID NO. 8 | β-Actin 3' | 5'-GTA CAC TGA CTT GAG ACC AGT TGA ATA AA-3' |
| PCR Probe | | |
| SEQ ID NO. 9 | Hum Uni | 5'-HEX-CAA GCT TCC CGT TCT CAG CC-BHQ-3'<br>5' Reporter Dye: HEX<br>3' Quencher: Black Hole Quencher 1 |

FIG. 11

| | 5'-End (5'-Tail) | Middle: Poly (A, C, G or T) | 3'-End ("Priming Nucleotides") |
|---|---|---|---|
| General Description | Absent, or random, about 1-100 nucleotides long, preferably with a binding sequence for an oligonucleotide, or mixtures thereof | Preferably poly (T); generally 15-50 nucleotides long, when poly T is then preferably 10-30 nucleotides long or mixtures thereof | Absent or preferably VVN-3', VN-3', or V-3', whereby V = A, C or G, and N = A, C, G or T |
| Anchor Oligonucleotide 1 | $N_{(n=14-34)}$ | Poly $(T)_{(n=10-30)}$ | VVN-3' |
| Anchor Oligonucleotide 2 | $N_{(n=14-34)}$ | Poly $(T)_{(n=10-30)}$ | VN-3' |
| Anchor Oligonucleotide 3 | $N_{(n=14-34)}$ | Poly $(T)_{(n=10-30)}$ | V-3' |
| Anchor Oligonucleotide 4 | Binding Sequence for Oligonucleotides | Poly $(T)_{(n=10-30)}$ | VVN-3 |
| Anchor Oligonucleotide 5 | Binding Sequence for Oligonucleotides that Comprise a Restriction Interface | Poly $(T)_{(n=10-30)}$ | VVN-3' |
| Anchor Oligonucleotide 6 | $N_{(n=14-34)}$ | Poly $(T)_{(n=10-30)}$ | VNN-3' |
| Anchor Oligonucleotide 7 (Example 1) | TGG AAC GAG ACG ACG ACA GAC CAA GCT TCC CGT TCT CAG CC | Poly $(T)_{(n=10-30)}$ | VVN-3' |
| Anchor Oligonucleotide 8 (Example 2) | AACGAGACGACGACAGAC | Poly $(T)_{(n=10-30)}$ | VN 3' |
| Anchor Oligonucleotide 9 (Example 3) | AACGAGACGACGACAGAC | Poly $(T)_{(n=10-30)}$ | V 3' |
| Anchor Oligonucleotide 10 (Example 4) | AACGAGACGACGACAGAC | Poly $(T)_{(n=10-30)}$ | N 3' |
| Anchor Oligonucleotide 11 (Example 5) | AACGAGACGACGACAGAC | Poly $(T)_{(n=10-30)}$ | NN 3' |
| Anchor Oligonucleotide 12 (Example 6) | AACGAGACGACGACAGAC | Poly $(T)_{(n=10-30)}$ | VNN 3' |

FIG. 12

| | | | |
|---|---|---|---|
| Anchor Oligonucleotide 13 (Example 7) | AACGAGACGACGACAGAC | Poly $(T)_{(n=10\text{-}30)}$ | VNNN 3' |
| Anchor Oligonucleotide 14 (Example 8) | AACGAGACGACGACAGAC | Poly $(T)_{(n=10\text{-}30)}$ | NNN 3' |
| Anchor Oligonucleotide 15 (Example 9) | TGG AAC GAG ACG ACG ACA GAC CAA GCT TCC CGT TCT CAG CC | Poly $(T)_{(n=10\text{-}30)}$ | VN 3' |
| Anchor Oligonucleotide 16 (Example 10) | TGG AAC GAG ACG ACG ACA GAC CAA GCT TCC CGT TCT CAG CC | Poly $(T)_{(n=10\text{-}30)}$ | VNN 3' |

FIG. 12 (Continued)

| | Uni Gap dT-VVN |
|---|---|
| Corn RNA | 30.65 |
| Corn RNA/miRNA | 20.61 |

| | Uni Gap dT-VVN | | Uni Gap dT-VN | | 2-Step Control |
|---|---|---|---|---|---|
| | +Additions | -Additions | +Additions | -Additions | |
| Corn RNA | No Ct | No Ct | No Ct | No Ct | N.D. |
| miRNA/Corn RNA | 33.23 | 28.44 | 25.54 | 29.30 | 29.67 |
| No CT: No Signal Detectable before PCR Cycle 40; N.D.: Not implemented | | | | | |

SEQUENCE LISTING

```
<160> NUMBER OF SEQ ID NOS: 27

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1

ugagguagua gguuguauag uu                                              22


<210> SEQ ID NO 2
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (65)..(65)
<223> OTHER INFORMATION: a, c, t, g, unknown or other
```

-continued

<400> SEQUENCE: 2
tggaacgaga cgacgacaga ccaagcttcc cgttctcagc cttttttttt ttttttttt 60 ttvvn 65

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3
aacgagacga cgacagac 18

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 4
gaggtagtag gttgtatag 19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
tggctcagtt cagcagga 18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
tagcagcaca taatggttt 19

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 7
tagcagcacg taaatattg 19

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8
gtacactgac ttgagaccag ttgaataaa 29

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9
caagcttccc gttctcagcc 20

<210> SEQ ID NO 10
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (42)..(71)
<223> OTHER INFORMATION: This region may encompass 10-30 nucleotides
<220> FEATURE:
<221> NAME/KEY: modified_base
<222> LOCATION: (74)..(74)
<223> OTHER INFORMATION: a, c, t or g

<400> SEQUENCE: 10
tggaacgaga cgacgacaga ccaagcttcc cgttctcagc cttttttttt ttttttttt 60 ttttttttt tvvn 74

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(48)
<223> OTHER INFORMATION: This region may encompass 10-30 nucleotides
<220> FEATURE:
<221> NAME/KEY: modified_base
<222> LOCATION: (50)..(50)
<223> OTHER INFORMATION: a, c, t or g

<400> SEQUENCE: 11
aacgagacga cgacagactt ttttttttt ttttttttt tttttttvn 50

<210> SEQ ID NO 12
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(48)
<223> OTHER INFORMATION: This region may encompass 10-30 nucleotides

<400> SEQUENCE: 12
aacgagacga cgacagactt ttttttttt ttttttttt ttttttttv 49

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(48)
<223> OTHER INFORMATION: This region may encompass 10-30 nucleotides
<220> FEATURE:
<221> NAME/KEY: modified_base
<222> LOCATION: (49)..(49)
<223> OTHER INFORMATION: a, c, t or g

<400> SEQUENCE: 13
aacgagacga cgacagactt tttttttttt tttttttttt ttttttttn 49

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(48)
<223> OTHER INFORMATION: This region may encompass 10-30 nucleotides
<220> FEATURE:
<221> NAME/KEY: modified_base
<222> LOCATION: (49)..(50)
<223> OTHER INFORMATION: a, c, t or g

<400> SEQUENCE: 14
aacgagacga cgacagactt tttttttttt tttttttttt ttttttttnn 50

<210> SEQ ID NO 15
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(48)
<223> OTHER INFORMATION: This region may encompass 10-30 nucleotides
<220> FEATURE:
<221> NAME/KEY: modified_base
<222> LOCATION: (50)..(51)
<223> OTHER INFORMATION: a, c, t or g

<400> SEQUENCE: 15
aacgagacga cgacagactt tttttttttt tttttttttt ttttttttvn n 51

<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(48)
<223> OTHER INFORMATION: This region may encompass 10-30 nucleotides
<220> FEATURE:
<221> NAME/KEY: modified_base
<222> LOCATION: (50)..(52)
<223> OTHER INFORMATION: a, c, t or g

<400> SEQUENCE: 16
aacgagacga cgacagactt tttttttttt tttttttttt ttttttttvn nn 52

<210> SEQ ID NO 17
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (19)..(48)
<223> OTHER INFORMATION: This region may encompass 10-30 nucleotides
<220> FEATURE:
<221> NAME/KEY: modified_base
<222> LOCATION: (49)..(51)
<223> OTHER INFORMATION: a, c, t or g

<400> SEQUENCE: 17
aacgagacga cgacagactt tttttttttt tttttttttt ttttttttnn n 51

<210> SEQ ID NO 18
<211> LENGTH: 73
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (42)..(71)
<223> OTHER INFORMATION: This region may encompass 10-30 nucleotides
<220> FEATURE:
<221> NAME/KEY: modified_base
<222> LOCATION: (73)..(73)
<223> OTHER INFORMATION: a, c, t or g

<400> SEQUENCE: 18
tggaacgaga cgacgacaga ccaagcttcc cgttctcagc cttttttttt tttttttttt 60
tttttttttt tvn 73

<210> SEQ ID NO 19
<211> LENGTH: 74
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (42)..(71)
<223> OTHER INFORMATION: This region may encompass 10-30 nucleotides
<220> FEATURE:
<221> NAME/KEY: modified_base
<222> LOCATION: (73)..(74)
<223> OTHER INFORMATION: a, c, t or g

<400> SEQUENCE: 19
tggaacgaga cgacgacaga ccaagcttcc cgttctcagc cttttttttt tttttttttt 60
tttttttttt tvnn 74

<210> SEQ ID NO 20
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
tttttttttt tt 12

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (6)..(25)
<223> OTHER INFORMATION: This region may encompass 11-20 nucleotides
<220> FEATURE:
<223> OTHER INFORMATION: See specification as filed for detailed description of substitutions and preferred embodiments

<400> SEQUENCE: 21
aaaaaaaaaa aaaaaaaaaa aaaaa 25

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(50)
<223> OTHER INFORMATION: This sequence may encompass 15-50 nucleotides
<220> FEATURE:
<223> OTHER INFORMATION: See specification as filed for detailed description of substitutions and preferred embodiments

<400> SEQUENCE: 22
tttttttttt tttttttttt tttttttttt tttttttttt tttttttttt 50

<210> SEQ ID NO 23
<211> LENGTH: 67
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(34)
<223> OTHER INFORMATION: This region may encompass 14-34 nucleotides
<220> FEATURE:
<221> NAME/KEY: modified_base
<222> LOCATION: (1)..(34)
<223> OTHER INFORMATION: a, c, t or g
<220> FEATURE:
<221> NAME/KEY: misc_feature
<222> LOCATION: (35)..(64)
<223> OTHER INFORMATION: This region may encompass 10-30 nucleotides
<220> FEATURE:
<221> NAME/KEY: modified_base
<222> LOCATION: (67)..(67)
<223> OTHER INFORMATION: a, c, t or g

<400> SEQUENCE: 23
nnnnnnnnnn nnnnnnnnnn nnnnnnnnnn nnnntttttt tttttttttt tttttttttt 60 ttttvvn 67

<210> SEQ ID NO 24

<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(34)
<223> OTHER INFORMATION: This region may encompass 14-34 nucleotides
<220> FEATURE:
<221> NAME/KEY: modified_base
<222> LOCATION: (1)..(34)
<223> OTHER INFORMATION: a, c, t or g
<220> FEATURE:
<221> NAME/KEY: misc_feature
<222> LOCATION: (35)..(64)
<223> OTHER INFORMATION: This region may encompass 10-30 nucleotides
<220> FEATURE:
<221> NAME/KEY: modified_base
<222> LOCATION: (66)..(66)
<223> OTHER INFORMATION: a, c, t or g

<400> SEQUENCE: 24
nnnnnnnnnn nnnnnnnnnn nnnnnnnnnn nnnntttttt tttttttttt tttttttttt 60 ttttvn 66

<210> SEQ ID NO 25
<211> LENGTH: 65
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(34)
<223> OTHER INFORMATION: This region may encompass 14-34 nucleotides
<220> FEATURE:
<221> NAME/KEY: modified_base
<222> LOCATION: (1)..(34)
<223> OTHER INFORMATION: a, c, t or g
<220> FEATURE:
<221> NAME/KEY: misc_feature
<222> LOCATION: (35)..(64)
<223> OTHER INFORMATION: This region may encompass 10-30 nucleotides

<400> SEQUENCE: 25
nnnnnnnnnn nnnnnnnnnn nnnnnnnnnn nnnntttttt tttttttttt tttttttttt 60 ttttv 65

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: misc_feature
<222> LOCATION: (1)..(30)
<223> OTHER INFORMATION: This region may encompass 10-30 nucleotides
<220> FEATURE:
<221> NAME/KEY: modified_base
<222> LOCATION: (33)..(33)
<223> OTHER INFORMATION: a, c, t or g

<400> SEQUENCE: 26
tttttttttt tttttttttt tttttttttt vvn 33

<210> SEQ ID NO 27

-continued

```
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(34)
<223> OTHER INFORMATION: This region may encompass 14-34 nucleotides
<220> FEATURE:
<221> NAME/KEY: modified_base
<222> LOCATION: (1)..(34)
<223> OTHER INFORMATION: a, c, t or g
<220> FEATURE:
<221> NAME/KEY: misc_feature
<222> LOCATION: (35)..(64)
<223> OTHER INFORMATION: This region may encompass 10-30 nucleotides
<220> FEATURE:
<221> NAME/KEY: modified_base
<222> LOCATION: (66)..(67)
<223> OTHER INFORMATION: a, c, t or g

<400> SEQUENCE: 27

nnnnnnnnnn nnnnnnnnnn nnnnnnnnnn nnnntttttt tttttttttt tttttttttt     60

ttttvnn                                                                67
```

METHOD OF POLYADENYLATION AND CDNA SYNTHESIS IN A SINGLE REACTION

The instant application contains a Sequence Listing which has been submitted via EFS-Web and is hereby incorporated by reference in its entirety. Said ASCII copy, created on Mar. 30, 2012, is named 05162US1 .txt and is 10,991 bytes in size.

BACKGROUND OF THE INVENTION

The invention relates to the field of molecular biology as well as the research in this field but also the human as well as non-human diagnosis.

The analysis of non-polyadenylated RNA molecules, such as, for example, bacterial RNAs or small RNAs, such as the so-called microRNAs (miRNAs), is made with difficulty and requires special processes. A possible process was recently described in the literature. This process comprises several enzymatic steps that are connected in succession, i.e., first a "tailing" of the RNA with poly-(A)-polymerase and a suitable substrate, typically ATP, is performed. Then, the poly-(A)-reaction is stopped, and the reaction product is purified. Then, the generated poly-(A)-RNA is added in a reverse transcriptase reaction and is converted with suitable primers into cDNA.

TECHNICAL FIELD

The performance of these two enzymatic reactions that are connected in succession is expensive in the implementation and has a number of error sources, for example input of nucleases, loss of material or pipetting errors.

microRNAs (miRNAs) vary in size from about 20 to 25 nucleotides and represent a new family of non-coding RNAs.

They are processed via a so-called "Hairpin Precursor" and can play a role as negative regulators in the gene expression. They thus adjust a number of genes downward (Ambros, V., 2001, MicroRNA's: Tiny Regulators with Great Potential, Cell 107, 823-826). miRNAs are first transcribed as long, "primary transcripts" (they are also referred to as primary miRNAs) (Lee, Y., Jeon, K. et al., 2002, MicroRNA Maturation: Stepwise Processing Subcellular Localisation, Embo J. 21, 4663-4670). These "primary transcripts" are then shortened, whereby the length resulting therefrom is in about 70 nucleotides. So-called "stem-loop structures" are produced; they are also referred to as "pre-miRNAs." Pre-miRNAs are exported in the cytoplasm. The exporting enzyme is named Exportin-5. They are further processed here, and in this way, an approximately 22-nucleotide-long, mature miRNA molecule is produced (Lee, Y., et al., 2003, The Nuclear RNA's III Drosha Initiates microRNA Processing, Nature 425, 415-419). The most recent studies have proposed that miRNAs play an important role in the development and differentiation. In principle, microRNAs can have a regulating action in two different ways. In plants, miRNAs complement with their corresponding mRNAs by exact complementarity. This leads to a destruction of the target-mRNA by a mechanism that comprises RNA interference (RNAi). In animals, miRNAs prevent gene expression by a mechanism, which comprises Lin-4 and Let-7. Here, the miRNAs are not exactly complementary to their corresponding mRNAs, but they prevent the synthesis and function of the proteins (Ambros, V., 2004, The Functions of Animal microRNAs, Nature, 431, 350-355). Because of the decisive role that the only recently discovered miRNAs play, their detection or analysis is of decisive importance.

In eukaryotes, the synthesis of the 18 s, 5.8 s and 25/28 s rRNAs comprises the processing in modifications of so-called precursor-rRNAs (pre-rRNA) in the nucleolus. This complex course of the rRNA biogenesis comprises many small so-called "small nucleolar RNAs" (snoRNA), which accumulate in the nucleolus. They do this in the form of so-called small nucleolar ribonucleo protein particles (snoRNPs) (Maxwell, E. S. et al., 1995, The Small Nucleolar RNAs, Annual Review Biochem, 35, 897-934).

All snoRNAs that are characterized to date, with the exception of the RNase MRP, fall into two families. The latter are the box c/D and box h/ACA slow RNAs, which can be distinguished by sequence motifs common thereto (Ballakin, A. D. et al., 1996, The RNA World of the Nucleolus: Two Major Families of Small Nucleolar RNAs Defined by Different Box Elements with Related Functions, Cell, 86, 823-834). The genomic organization of the snoRNA genes has a large diversity in various eukaryotes. In vertebrates, most snoRNAs are introduced within Introns via "host genes." Exceptions such as U3 are independently transcribed. In yeast, there are snoRNAs that are introduced into Introns, but the majority of the snoRNAs are transcribed as single genes with a separate promoter. Clustered snoRNA genes are transcribed upstream by common promoters. Based on the small sizes and the deficient polyadenylation, the detection or the analysis of snoRNAs is a molecular-biological challenge.

The PCR is a frequently-used instrument for the study of microbial organisms and is also used, i.a., to analyze 16S rRNA genes. However, the discovery of new genes in microbial samples is limited by the only conditionally possible synthesis of primers. Thus, primers are derived for 16S RNA genes from those sequences that are already known from cultivated microbes (Olson, D. J., 1986, Microbial Ecology and Evolution: A Ribosomal RNA Approach, Annu. Rev. Microbial. 40: 337-365). Based on the systematics that there is recourse to sequences that are already known namely for the extraction of 16S rRNA genes from organisms that are unknown to date, it is probable that the microbial diversity is greatly underestimated and also not isolated.

Just as the 16S rRNA molecules can only be isolated with difficulty, prokaryotic mRNA molecules can be isolated with difficulty owing to a lack of knowledge of the sequence and in particular owing to a lack of poly-A-tail.

The prior art knows a 2-stage process. In this process, an RNA molecule is reacted with the aid of the enzyme poly-A-polymerase and the substrate adenosine triphosphate, such that a polyadenylated ribonucleic acid molecule is produced. This thus polyadenylated ribonucleic acid molecule is purified in an additional step before a reverse transcription takes place in a third step. Reverse transcription is appropriated in the polyadenylated tail, whereby a homopolymer oligonucleotide in general attaches a poly-T-oligonucleotide to the polyadenylated RNA tail in a complementary manner. The 3'-end of the poly-T-oligonucleotide is now used by the polymerase to produce a deoxyribonucleic acid strand, which is complementary to the existing ribonucleic acid strand. The thus produced strand is named "first strand of cDNA." This cDNA can be used in a PCR reaction, whereby it results in the use of either random primers or else specific primers to generate an amplificat. Shi et al. teaches especially the miRNA detection via an oligo-dT adapter-primer, whereby an adapter of the specific primer is used in the PCR (Shi, R., and Chiang, V. L. (Shi, R. et al., Facile Means for Quantifying microRNA Expression by Real-Time PCR, Biotechniques, 2005, 39, 519-25).

This only recently published process has decisive drawbacks relative to the above-mentioned special ribonucleic acid molecules.

Thus, the two-stage process in general may involve an introduction of contaminants. The purification step leads to losses of rare RNAs. The two-stage process requires an inactivation of the first enzyme as well as an incubation time for the first enzyme and the second enzyme, which together results in a very great time expenditure. In addition, the two-stage process has the drawback that a danger of confusion of samples can then occur when two or more samples are treated at the same time. As is known from the prior art, ribonucleic acids are relatively sensitive as far as the attack of nucleases is concerned. The two-stage process, in particular the step of purification after the first process, involves the danger that nucleases are introduced. Ultimately, two or more steps always lead to the fact that the danger of pipetting errors increases.

SUBJECT OF THE INVENTION

It is thus the object of this invention to prepare a process that makes possible the cDNA synthesis, prevents contaminants as much as possible, is less time-consuming, minimizes the danger of confusion of the samples, minimizes the danger of the introduction of nucleases, and finally excludes the danger of pipetting errors as much as possible.

This object is achieved by a process for synthesis of a cDNA in a sample, in an enzymatic reaction, whereby the process comprises the following steps:

(a) Simultaneous preparation of a first enzyme with polyadenylation activity, a second enzyme with reverse transcriptase activity, a buffer, at least one ribonucleotide, at least one deoxyribonucleotide, an anchor oligonucleotide, (b) addition of a sample that comprises a ribonucleic acid, and (c) incubation of the agents of steps (a) and (b) in one or more temperature steps, which are selected such that the first enzyme and the second enzyme show activity.

Up until today, there have been concerns about a combination of the enzymatic polyadenylation and the reverse transcriptase being technically possible. This is shown in that even more recently, i.e., after discovery of microRNAs and snoRNAs, which represent a special molecular-biological challenge as regards analysis and isolation, the enzymatic reactions were always performed in succession (Want, J. F., et al., Identification of 20 microRNAs from Oryza sativa, Nucleic Acid Res., 2004, 32, 1688-95; Shi, R. and Chiang, V. L., Facile Means for Quantifying microRNA Expression by Real-Time PCR, Biotechniques, 2005, 39, 519-25; Fu, H., et al., Identification of Human Fetal Liver miRNAs by a Novel Method; FEBS Lett, 2005, 579, 3849-54; Chen, C. L. et al., The High Diversity of snoRNAs in Plants: Identification and Comparative Study of 120 snoRNA Genes from Oryza Sativa, Nucleic Acids Res, 2003, 31, 2601-13; Botero, L. M. et al., Poly(A) Polymerase Modification and Reverse Transcriptase PCR Amplification of Environmental RNA, Appl. Environ Microbiol, 2005, 71, 1267-75). Surprisingly enough, both processes, i.e., the polyadenylation and reverse transcription, have already been known to one skilled in the art for a long time (Sano, H., and Feix, G., Terminal Riboadenylate Transferase from *Escherichia coli*. Characterization and Application, Eur. J. Biochem., 1976, 71, 577-83). In general, according to the poly-A-tailing step, one skilled in the art has purified the reaction product (Shi, R., et al., Facile Means for Quantifying microRNA Expression by Real-Time PCR, Biotechniques, 2005, 39, 519-25). The reason for this lies both in the clearly different compositions of the reaction buffers and the substrates that are required for the reaction.

Another subject of this invention is to prepare a simple process that makes the cDNA synthesis possible and couples this reaction optionally with a third enzymatic reaction, which allows the specific detection of the generated cDNA in the same reaction vessel. By a very simple handling, this "3-in-1" process shows special advantages when a large number of samples are to be analyzed in one or a few analytes. The reason is that, e.g., coupled to a real-time PCR, a very quick and simple process shows a large number of samples to be analyzed. Additional handling steps and contaminations are to be prevented as much as possible, by which it is less time-consuming, the danger of confusion of the samples is minimized, the danger of the introduction of nucleases is minimized, and ultimately, the danger of pipetting errors is excluded as much as possible.

The object of the "3-in-1" reaction is achieved by a process for the synthesis of a cDNA in a sample, in an enzymatic reaction, followed by another enzymatic reaction, optionally an amplification, optionally coupled to the detection, either in real-time during the amplification or downstream, whereby the process comprises the following steps: (a) simultaneous preparation of a first enzyme with polyadenylation activity, a second enzyme with reverse transcriptase activity, a buffer, at least one ribonucleotide, at least one deoxyribonucleotide, an anchor oligonucleotide, at least a third enzyme with nucleic acid-synthesis activity, at least one primer, and optionally a probe, (b) addition of a sample that comprises a ribonucleic acid, and (c) incubation of the agents of steps (a) and (b) in one or more temperature steps, which are selected such that the first and second enzyme show activity, and optionally the third enzyme is active or inactive. Optionally, one or more temperature steps follow, in which the first and second enzymes are less active or inactive, and the third enzyme is active.

The substrate of the poly-(A)-polymerase that is used in vivo is adenosine triphosphate (ATP). For some poly-(A)-polymerases, it was shown that even attaching a short tail to other NTPs as a substrate can be possible (Martin, G., and Keller, W., Tailing and 3'-End Labeling of RNA with Yeast Poly(A) Polymerase and Various Nucleotides, RNA, 1998, 4, 226-30).

Surprisingly enough, the inventors of this invention had discovered that it is possible, under certain requirements, to be able to execute the two still very different enzymatic reactions simultaneously in one reaction vessel. In a preferred embodiment of the invention, the sample is a ribonucleic acid, which is selected from the group that comprises prokaryotic ribonucleic acids, eukaryotic ribonucleic acids, viral ribonucleic acids, ribonucleic acids whose origin is an archaeorganism, microribonucleic acids (miRNA), small nucleolar ribonucleic acids (snoRNA), messenger ribonucleic acid (mRNA), transfer-ribonucleic acids (tRNA), non-polyadenylated ribonucleic acids in general, as well as ribosomal ribonucleic acids (rRNA). Moreover, a mixture of two or more of the above-mentioned ribonucleic acids. In the sample, of course, poly-A RNA can also already be contained.

In an especially preferred embodiment of this invention, the sample is a ribonucleic acid, which is selected from the group that comprises prokaryotic ribonucleic acids, miRNA, snoRNA and rRNA. In the most preferred embodiment of this invention, the sample comprises a ribonucleic acid, which is selected from the group that comprises miRNA and snoRNA. Other mixed samples that consist of different amounts of ribonucleic acids of different types associated with other substances are preferred.

In addition, the inventors of this invention have discovered that it is possible, under certain conditions, to be able to execute the two still very different enzymatic reactions simultaneously in one reaction vessel as well as to couple the latter in addition to a third enzymatic reaction for specific detection of the generated cDNA, which is preferably a nucleic acid-synthesis activity. In a preferred embodiment of the invention, the sample is a ribonucleic acid, which is selected from the group that comprises prokaryotic ribonucleic acids, eukaryotic ribonucleic acids, viral ribonucleic acids, ribonucleic acids whose origin is an archae-organism, microribonucleic acids (miRNA), small nucleolar ribonucleic acids (snoRNA), messenger ribonucleic acid (mRNA), transfer-ribonucleic acids (tRNA), and non-polyadenylated ribonucleic acids in general, as well as ribosomal ribonucleic acids (rRNA). Moreover, a mixture of two or more of the above-mentioned ribonucleic acids. In the sample, of course, poly-A RNA can also already be contained.

In an especially preferred embodiment of this invention, the sample is a ribonucleic acid that is selected from the group that comprises prokaryotic ribonucleic acids, miRNA, snoRNA and rRNA. In the most preferred embodiment of this invention, the sample comprises a ribonucleic acid, which is selected from the group that comprises miRNA and snoRNA. Other mixed samples that consist of different amounts of ribonucleic acids of different types associated with other substances are preferred.

Based on these advantages of the process according to the invention, the inventors could show that it is possible to prepare and to characterize miRNAs efficiently and without contamination.

In one embodiment of the invention, the anchor oligonucleotide is a homopolymer oligonucleotide, which is selected from the group that comprises a poly-(A)-oligonucleotide, poly-(C)-oligonucleotide, poly-(T)-oligonucleotide, poly-(G)-oligonucleotide, poly-(U)-oligonucleotide, poly-(A)-oligonucleotide additionally comprising a 5'-tail, poly-(C)-oligonucleotide additionally comprising a 5'-tail, poly-(T)-oligonucleotide additionally comprising a 5'-tail, poly-(G)-oligonucleotide additionally comprising a 5'-tail and poly-(U)-oligonucleotide additionally comprising a 5'-tail. A poly-(T)-oligonucleotide, which optionally, as already explained above, additionally can have a 5'-tail, is preferred.

The anchor oligonucleotide according to the invention is generally between 6 and 75 nucleotides long. However, it can be up to about 150 nucleotides long. If the anchor oligonucleotide is synthetic, the maximum length follows from the technical limitations of the DNA synthesis. The anchor oligonucleotide optionally comprises a 5'-tail and/or an anchor sequence. A 5'-tail is an additional nucleotide sequence on the 5'-end of the oligonucleotide, which is used, for example, to introduce a cloning sequence, primer and/or probe-binding sites or any other sequence. The identification of suitable sequences for the 5'-tail is possible for one skilled in the art based on the requirements of the respective application.

On the 3'-end of the anchor oligonucleotide, an additional anchor sequence, typically with a length of one to five additional nucleotides, can be contained. The anchor sequence can have a length of at least one base, whereby the first position in a preferred embodiment is a degenerated base, which contains all bases except for the base that is used in the homopolymer portion of the anchor oligonucleotide. After that, other bases can follow. The latter can also be degenerated. In one preferred embodiment here, the use of N wobbles is useful, whereby N=A, C, G, T or corresponding analogs.

Normally, the anchor oligonucleotide is a deoxyribonucleic acid (DNA). The anchor oligonucleotide, however, can also be a peptide nucleic acid (PNA). Locked nucleic acids (LNA), phosphorus thioate-deoxyribonucleic acids, cyclohexene-nucleic acids (CeNA), N3'-P5'-phosphoramedites (NP), and tricyclo-deoxyribonucleic acids (tcDNA) are also possible. An anchor oligonucleotide, which is a deoxyribonucleic acid (DNA), is preferred, however. Mixtures of RNA and DNA or one or more of the modified nucleic acids or analogs, as well as other modifications, such as corresponding base analogs, which are able to hybridize with RNA or DNA under the selected conditions, are possible. In one especially preferred embodiment, the anchor oligonucleotide is a poly-(T)-oligonucleotide, which additionally comprises a 5'-tail, is a deoxyribonucleic acid, is 15-150 nucleotides long, and is present as a mixture. On the 3'-end of the anchor oligonucleotide, an additional anchor sequence typically with a length of one to five additional nucleotides can be contained. The anchor sequence can have a length of at least one base, whereby the first position in a preferred embodiment is a degenerated base, which contains all bases except for the base that is used in the homopolymer portion of the anchor oligonucleotide. After that, other bases can follow. The latter can also be degenerated. Here, in a preferred embodiment, the use of N wobbles is useful, whereby N=A, C, G, T or corresponding analogs.

By way of example, the following anchor oligonucleotides according to the invention can be mentioned:

Example 1 (SEQ ID NO: 10):
5' TGG AAC GAG ACG ACG ACA GAC CAA GCT TCC CGT TCT CAG CC $(T)_x$VVN 3'

Example 2 (SEQ ID NO: 11):
5' AACGAGACGACGACAGAC$(T)_x$VN 3'

Example 3 (SEQ ID NO: 12):
5' AACGAGACGACGACAGAC$(T)_x$V 3'

Example 4 (SEQ ID NO: 13):
5' AACGAGACGACGACAGAC$(T)_x$N 3'

Example 5 (SEQ ID NO: 14):
5' AACGAGACGACGACAGAC$(T)_x$NN 3'

Example 6 (SEQ ID NO: 15):
5' AACGAGACGACGACAGAC$(T)_x$VNN 3'

Example 7 (SEQ ID NO: 16):
5' AACGAGACGACGACAGAC$(T)_x$VNNN 3'

Example 8 (SEQ ID NO: 17):
5' AACGAGACGACGACAGAC$(T)_x$NNN 3'

Example 9 (SEQ ID NO: 18):
5' TGG AAC GAG ACG ACG ACA GAC CAA GCT TCC CGT TCT CAG CC$(T)_x$VN 3'

Example 10 (SEQ ID NO: 19):
5' TGG AAC GAG ACG ACG ACA GAC CAA GCT TCC CGT TCT CAG CC$(T)_x$VNN 3'

X is preferably 10 to 30 bases.

V and N are from the single letter code for degenerate bases, V=A, C, G; N=A, C, G, T.

The identification of other suitable 5'-tail sequences is possible to one skilled in the art.

The optional 5'-tail comprises additional 1-100 nucleotides, which can be used for the following analyses. Thus, in a preferred embodiment, the 5'-tail can contain the binding sequence for an oligonucleotide, such as, e.g., one or more DNA probes and/or one or more PCR primers. The sequences that are used for the 5'-tail are preferably selected such that the latter are compatible with the process according to the invention. This comprises, e.g., the selection of those sequences that do not cause any undesirable secondary reactions, both in the process according to the invention and in the subsequent analysis process.

According to the invention, anchor oligonucleotides are shown in FIG. 12.

In principle, the enzymatic reaction according to the invention can take place on a vehicle or in a container, i.e., the reaction can take place in a reaction vessel. Such a reaction vessel can be a reaction tube or, for example, a microtiter plate. The reaction can take place on a chip. If it takes place on a chip, one or more components can be immobilized. The reaction can take place on a test strip or in a microfluidic system. The most varied embodiments relative to the vehicle or container are known to one skilled in the art.

In a preferred embodiment, the ribonucleotide is an adenosine-5'-triphosphate, a thymidine-5'-triphosphate, a cytosine-5'-triphosphate, a guanine-5'-triphosphate and/or a uracil-5'-triphosphate. The ribonucleotide can also be a base analog. The ribonucleotide can be modified or labeled. In principle, it is essential that the ribonucleotide can be reacted by the enzyme in the polyadenylation activity as substrate.

The deoxyribonucleotide according to the invention can be selected from the group that comprises a deoxyadenosine-5'-triphosphate (dATP), a deoxythymine-5'-triphosphate (dTTP), a deoxycytosine-5'-triphosphate (dCTP), a deoxyguanosine-5'-triphosphate (dGTP), a deoxyuracil-5'-triphosphate (dUTP) as well as modified deoxyribonucleotides and labeled deoxyribonucleotides. Applications are also conceivable in which in addition to or in exchange, one or more deoxyribonucleotides, which contain a universal base or a base analog, are used. It is essential for the implementation of the invention that the deoxyribonucleotides that are used allow a cDNA synthesis.

According to the invention, it is preferred if dATP, dCTP, dTTP, and dGTP are present together as a mixture.

According to the invention, deoxyuracil-5'-triphosphate can also be used in the mixture. This can be combined with an enzymatic reaction that takes place after the actual reaction and that uses the uracil-DNA-glycosilase and cannot degrade further used enzymatically produced reaction product.

If a deoxyribonucleotide is labeled, the labeling can be selected from the group that comprises $^{32}P$, $^{33}P$, $^{35}S$, $^{3}H$; a fluorescent dye, such as, for example, fluorescein isothiocyanate (FITC), 6-carboxyfluorescein (FAM), xanthene, rhodamine, 6-carboxy-2',4',7',4,7-hexachlorofluorescein (HEX), 6-carboxy-4',5'-dichloro-2',7'-dimethoxy fluorescein (JOE), N,N,N',N'-tetramethyl-6-carboxyrhodamine (TAMRA), 6-carboxy-X-rhodamine (ROX), 5-carboxyrhodamine-6G (R6G5), 6-carboxyrhodamine-6G (RG6), rhodamine 110; coumarins, such as umbelliferones; benzimides, such as Hoechst 33258; phenanthridines, such as Texas Red, ethidium bromides, acridine dyes, carbazole dyes, phenoxazine dyes, porphyrine dyes, polymethine dyes; cyanine dyes, such as Cy3, Cy5, Cy7, BODIPY dyes, quinoline dyes and alexa dyes. Other labels such as the inclusion of biotin or one or more haptens, such as, e.g., digoxigenin, which allow a direct or indirect detection of the nucleic acid. Indirect detection, such as, e.g., via antibodies, which in turn, e.g., enzymatic detection via an enzyme coupled to an antibody. Also, via the introduction of nanoparticles, which are coupled to, e.g., antibodies or an affinity ligand, an indirect detection is possible.

A modification of the deoxyribonucleotide can also be carried out via the 5'-phosphate, which allows a simpler cloning. By including reactive groups, such as, e.g., an amino linker (also biotin), the deoxyribonucleotide can be, e.g., immobilized, or a direct or indirect detection can be made available.

Especially preferred modifications are selected from the group that comprises fluorescence dyes, haptens, 5'-phosphate, 5'-biotin, and 5'-amino linkers.

According to the invention, the concentration of a deoxyribonucleotide in the reaction is at least 0.01 mmol and at most 10 mmol. This concentration information is the concentration of the individual deoxyribonucleotide. In one of the preferred embodiments, the deoxyribonucleotides, in each case dATP, dCTP, dGTP and dTTP, are present at a concentration of 0.2 mmol to 2 mmol. This concentration information is the concentration of the individual deoxyribonucleotide in the mixture. In an especially preferred embodiment of the invention, the individual deoxyribonucleotide, dATP, dCTP, dGTP and dTTP, is present at a concentration of 0.5 mmol in each case.

Surprisingly enough, the inventors have determined that the one-step enzyme reaction, as it is the subject of this invention, can take place in a narrow buffer-pH range of 6 to 10 with the presence of magnesium ions ($Mg^{2+}$). Thus, a pH of 6 to 10 is present in a preferred embodiment.

In an especially preferred embodiment, the buffer according to the invention has a pH of 6.8 to 9.

In another embodiment of the invention according to the invention, the buffer according to the invention comprises additional ions, which can be selected from the group that comprises $Mn^{2+}$, $K^{+}$, $NH^{4+}$, and $Na^{+}$.

Buffers according to the invention contain, for example, $MgCl_2$, $MgSO_4$, magnesium acetate, $MnCl_2$, KCl, $(NH_4)_2SO_4$, $NH_4Cl$, and NaCl. As buffer substances, tris, tricine, bicine, HEPES, as well as other buffer substances that are in the pH range according to the invention or mixtures of two or more appropriate buffer substances are suitable.

A number of enzymes with polyadenylation activity are known to one skilled in the art. According to the invention, the latter are selected from the group that comprises enzymes of prokaryotic origin, eukaryotic origin, viral origin and archae origin as well as also enzymes of plant origin.

A polyadenylation activity in terms of this invention is an enzymatic activity that uses the 3'-end of a ribonucleic acid as a substrate and is able to add enzymatic ribonucleotides, specifically preferably at least 10 to 20 ribonucleotides, to this 3'-end in a suitable buffer. In a preferred embodiment, the enzyme is an enzyme that is able to use adenosine-5'-triphosphate as a substrate. According to the invention, the latter comprises enzymes and reaction conditions that have a polyadenylation activity in terms of the invention when using single-strand and double-strand RNA, e.g., hairpin RNA, such as, e.g., pre-miRNA. Based on the RNA to be analyzed, one skilled in the art can select enzymes and reaction conditions such that either single-strand RNAs (e.g., mature miRNAs), or double-strand RNAs (e.g., pre-miRNAs) or both are made available for analysis.

In general, a polyadenylation activity in terms of the invention is a transcriptase activity.

In a preferred embodiment, the enzyme with polyadenylation activity is an enzyme that is selected from the group that comprises poly-(A)-polymerase from *Escherichia coli*, poly-(A)-polymerase from yeast, poly-(A)-polymerase from cattle, poly-(A)-polymerase from frogs, human poly-(A)-polymerase, and plant poly-(A)-polymerase. Others are known to one skilled in the art or can be newly identified by the analysis of homology in known poly-(A)-polymerases. In an especially preferred embodiment, the enzyme with polyadenylation activity is a poly-(A)-polymerase from *Escherichia coli.*

The enzyme with reverse transcriptase activity according to the invention is selected according to the invention from the group that comprises enzymes from viruses, bacteria, archaebacteria and eukaryotes, in particular from thermostable organisms. These also include, e.g., enzymes from Introns, retrotransposons or retroviruses. An enzyme with reverse transcriptase activity is an enzyme, according to the invention, which is able to incorporate deoxyribonucleotides in a complementary way in a ribonucleic acid on the 3'-end of a deoxyoligonucleotide or ribooligonucleotide that is hybridized on the ribonucleic acid under suitable buffer conditions. This comprises, on the one hand, enzymes that of course have this function but also enzymes that obtain such a function only by changing their gene sequence, such as, e.g., mutagenesis, or by corresponding buffer conditions.

Preferred is the enzyme with reverse transcriptase activity, an enzyme that is selected from the group that comprises HIV Reverse Transcriptase, M-MLV Reverse Transcriptase, EAIV Reverse Transcriptase, AMV Reverse Transcriptase, *Thermus thermophilus* DNA polymerase I, M-MLV RNAse H, Superscript, Superscript II, Superscript III, MonsterScript (Epicenter), Omniscript, Sensiscript Reverse Transcriptase (Qiagen), ThermoScript and Thermo-X (both Invitrogen). According to the invention, enzymes can also be used that as enzymes have reverse transcriptase only after a modification of the gene sequence. A reverse transcriptase activity that has elevated accuracy can also be used. By way of example, e.g., AccuScript Reverse Transcriptase (Stratagene) can be mentioned here. It is evident to one skilled in the art that even the use of mixtures of two or more enzymes with reverse transcriptase activity is possible.

It is known to one skilled in the art that most enzymes with reverse transcriptase activity require a divalent ion. Thus, in a preferred embodiment as already described above, a divalent ion is present in those enzymes that require a divalent ion. $Mg^{2+}$ and $Mn^{2+}$ are preferred.

Preferred combinations of enzymes are HIV Reverse Transcriptase or M-MLV Reverse Transcriptase or EAIV Reverse Transcriptase or AMV Reverse Transcriptase or *Thermus thermophilus* DNA polymerase I or M-MLV RNAse H, Superscript, Superscript II, Superscript III or MonsterScript (Epicenter) or Omniscript Reverse Transcriptase (Qiagen) or Sensiscript Reverse Transcriptase (Qiagen), ThermoScript, Thermo-X (both Invitrogen) or a mixture of two or more enzymes with reverse transcriptase activity and poly-(A)-polymerase from *Escherichia coli*. In addition, HIV Reverse Transcriptase or M-MLV Reverse Transcriptase or EAIV Reverse Transcriptase or AMV Reverse Transcriptase or *Thermus thermophilus* DNA Polymerase I or M-MLV RNAse H, Superscript, Superscript II, Superscript III or MonsterScript (Epicenter) or Omniscript Reverse Transcriptase (Qiagen) or Sensiscript Reverse Transcriptase (Qiagen), ThermoScript, Thermo-X (both Invitrogen) or a mixture of two or more enzymes with reverse transcriptase activity and poly-(A)-polymerase from yeast.

It is known to one skilled in the art that high temperatures in reverse transcription have the effect that problems with secondary structures do not play a decisive role. Moreover, high temperatures in certain enzymes have the effect that the specificity of reverse transcription increases such that false pairs and false priming are suppressed. Thus, a reverse transcriptase, which is thermophilic, is used in an embodiment of this invention. An enzyme that has an optimum nucleic acid synthesis activity at between 45° C. and 85° C. is preferred, more preferred between 55° C. and 80° C., and most preferred between 60° C. and 75° C. *Thermus thermophilus* (Tth) DNA polymerase I is preferred.

If the enzyme with polyadenylation activity is a non-thermophilic enzyme and the enzyme with reverse transcriptase activity is a thermophilic enzyme, the process can be carried out in several temperature steps according to the invention, whereby the first temperature step allows a temperature to be used that is the optimum temperature for the enzyme with polyadenylation activity, and the second temperature step allows a temperature to be used that is the optimum temperature for the enzyme with reverse transcriptase activity.

If, for example, the AMV reverse transcriptase is used, the second temperature step takes place at 42° C., while the first temperature step, which has primarily the activity of the enzyme with polyadenylation activity, takes place at a temperature of 37° C. Implementation at a constant temperature is also possible, however.

One skilled in the art is able to select the temperatures so that the respective enzyme activities have an impact. If, for example, a combination of poly-(A)-polymerase from *Escherichia coli* accompanied by DNA polymerase from *Therms thermophilus* is used, the course of the temperatures appears as follows: first, it is incubated at 37° C. and then at 55 to 70° C. According to the invention, a non-thermostable enzyme can thus be combined with a thermostable enzyme. In this case, the temperature steps then depend on which of the two enzymes has polyadenylation activity. According to the invention, it is preferred that the enzyme with reverse transcriptase reactivity be thermostable. In the opposite case, and this is plausible to one skilled in the art, it may be that by the incubation at a higher temperature in the polyadenylation step, the enzyme with reverse transcriptase activity is partially or completely inactivated. Thus, it is also preferred if the two enzymes are thermostable.

In addition, it is known to one skilled in the art that the enzymes are processive to very different degrees, so that one skilled in the art can combine enzymes with different processivity in such a way that templates of varying lengths are readily converted into cDNA in different ways. By using corresponding amounts of the respective enzymes, of one or more suitable incubation temperatures and incubation times, it is possible for one skilled in the art to achieve satisfactory results.

The process according to the invention preferably comprises additional poly-(C)-polynucleotides. The process according to the invention especially preferably comprises additional poly-(C)-polyribonucleotides. Preferably, 1 ng to 300 ng of poly-(C)-polyribonucleotides for each 20 μl is incorporated, preferably 10 ng to 150 ng of poly-(C)-polyribonucleotides for each 20 μl of reaction is incorporated, especially preferably 25 ng to 100 ng of poly-(C)-polyribonucleotides for each reaction is incorporated, and most preferably 50 ng to 75 ng of poly-(C)-polyribonucleotides for each 20 μl of reaction is incorporated.

The reaction according to the invention can comprise additional reagents, such as, for example, volume excluder, a single-strand binding protein, DTT and/or competitor nucleic acids.

If a volume excluder is used, the latter is selected from the group that comprises dextran, and polyethylene glycol, and in EP 1411133A1, volume excluders according to the invention are mentioned.

In a preferred embodiment, the competitor-nucleic acid is a homopolymer ribonucleic acid, most preferably polyadenoribonucleic acid. Examples are disclosed in U.S. Pat. No. 6,300,069.

The process according to the invention preferably comprises additional poly-(C)-polynucleotides. The process according to the invention especially preferably comprises additional poly-(C)-polyribonucleotides. Preferably, 1 ng to 300 ng of poly-(C)-polyribonucleotides is incorporated for each 20 μl; preferably 10 ng to 150 ng of poly-(C)-polyribonucleotides is incorporated for each 20 μl of reaction; especially preferably, 25 ng to 100 ng of poly-(C)-polyribonucleotides is incorporated for each reaction; and most preferably 50 ng to 75 ng of poly-(C)-polyribonucleotides is incorporated for each 20 μl of reaction.

It is obvious to one skilled in the art that it may be advantageous to prevent the competitor-nucleic acid itself from being used as a substrate for the poly-(A)-polymerase activity. A possible solution is the blocking of the 3' OH group of the competitor-nucleic acid. Corresponding solutions, such as, e.g., use of a 3' phosphate, incorporation of a dideoxynucleotide or reverse bases, are known to one skilled in the art.

It is also obvious to one skilled in the art that it is advantageous to be able to prevent the competitor-nucleic acid itself from being used as a substrate for the reverse transcriptase activity. This can be ensured by selecting a competitor-nucleic acid that cannot be converted into cDNA under the given reaction conditions, e.g., since the primers that are used cannot hybridize onto the latter. Another possible solution is the blocking of the 3' OH group of the competitor-nucleic acid. Corresponding solutions, such as, e.g., use of a 3' phosphate, incorporation of a dideoxynucleotide or reverse bases, are known to one skilled in the art.

In addition, the invention relates to a reaction mixture that comprises a first enzyme with polyadenylation activity, a second enzyme with reverse transcriptase activity, optionally a buffer, optionally at least one ribonucleotide, optionally at least one deoxyribonucleotide and optionally one anchor oligonucleotide. The anchor oligonucleotide preferably comprises a homopolymer portion, an anchor sequence and/or a tail. The reaction mixture additionally preferably comprises random primers. The additional use of random primers has the advantage that even 5'-ends of long transcripts are efficiently converted, which is important in quantitative analyses. The reaction mixture can contain the same agents as are used for the process according to the invention.

In an embodiment of the invention, the anchor oligonucleotide is a homopolymer oligonucleotide, which is selected from the group that comprises a poly-(A)-oligonucleotide, poly-(C)-oligonucleotide, poly-(T)-oligonucleotide, poly-(G)-oligonucleotide, poly-(U)-oligonucleotide, poly-(A)-oligonucleotide additionally comprising a 5'-tail, poly-(C)-oligonucleotide additionally comprising a 5'-tail, poly-(T)-oligonucleotide additionally comprising a 5'-tail, poly-(G)-oligonucleotide additionally comprising a 5'-tail and poly-(U)-oligonucleotide additionally comprising g a 5'-tail. Preferred is a poly-(T)-oligonucleotide, which optionally in addition can have a 5'-tail as already explained above.

The anchor oligonucleotide according to the invention is generally between 6 and 75 nucleotides long. It can be up to about 150 nucleotides long, however. If the anchor oligonucleotide is synthetic, the maximum length is produced from the technical limitations of the DNA synthesis. The anchor oligonucleotide optionally comprises a 5'-tail and/or an anchor sequence. A 5'-tail is an additional nucleotide sequence on the 5'-end of the oligonucleotide, which, for example, in this case is used to insert a cloning sequence, primer and/or probe-binding sites, or any other sequence. The identification of suitable sequences for the 5'-tail is possible for one skilled in the art based on the requirements of the respective application.

At the 3'-end of the anchor oligonucleotide, an additional anchor sequence typically can be contained with a length of one to five additional nucleotides. The anchor sequence can have a length of at least one base, whereby the first position in a preferred embodiment is a degenerated base, which contains all bases except for the base that is used in the homopolymer portion of the anchor oligonucleotide. Then, additional bases can follow. The latter can also be degenerated. In a preferred embodiment, the use of N wobbles is useful here, whereby N=A, C, G, T or corresponding analogs.

The optional 5'-tail additionally comprises 1-100 nucleotides, which can be used for subsequent analyses. Thus, in a preferred embodiment, the 5'-tail can contain the binding sequence for an oligonucleotide, such as, e.g., one or more DNA probes and/or one or more PCR primers. The sequences that are used for the 5'-tail are preferably selected such that the latter are compatible with the process according to the invention. This comprises, e.g., the selection of those sequences that do not cause any undesirable secondary reactions, both in the process according to the invention and in subsequent analytical processes.

The reaction mixture according to the invention comprises the anchor oligonucleotide according to the invention, which has a length of between 10 and 150 nucleotides, and optionally at the 3'-end, carries an anchor sequence according to the invention that is one to five nucleotides long. The reaction mixture according to the invention comprises the anchor oligonucleotide, which, as described above, for example, is a deoxyribonucleic acid (DNA), a peptide nucleic acid (PNA) or a locked nucleic acid (LNA). In a preferred embodiment, the reaction mixture according to the invention comprises an anchor oligonucleotide according to the invention, which is a poly-(T)-oligonucleotide and in addition carries a 5'-tail, whereby the oligonucleotide is a deoxyribonucleic acid, which is 10 to 75 nucleotides long and is present as a mixture, whereby on the 3'-end, an anchor sequence is present, consisting of one nucleotide in each case, which is selected from the group that comprises A, G and C, optionally followed by one to five additional nucleotides that comprise all four bases A, C, G and T or corresponding analogs.

Anchor oligonucleotides of the reaction mixture according to the invention are shown in FIG. 12.

The reaction mixture according to the invention also comprises at least one ribonucleotide as they were described above for the process according to the invention. In particular, the reaction mixture according to the invention comprises at least one ribonucleotide that is selected from ATP, TTP, CTP, GTP, UTP or corresponding base analogs. The ribonucleotides can optionally be modified or labeled as described above. The reaction mixture according to the invention comprises deoxyribonucleotides, as it was described for the process according to the invention. In particular, the reaction mixture according to the invention comprises one or more deoxyribonucleotides, such as, for example, dATP, dCTP, dGTP, dUTP, and/or dTTP. In a preferred embodiment, a mixture of deoxyribonucleotides, which allow a cDNA synthesis, is used. These deoxyribonucleotides can optionally be modified or labeled.

If a deoxyribonucleotide of the reaction mixture according to the invention is labeled, the labeling can be selected from the group that comprises $^{32}P$, $^{33}P$, $^{35}S$, $^{3}H$, a fluorescent dye such as, for example, fluorescein isothiocyanate (FITC), 6-carboxyfluorescein (FAM), xanthene, rhodamine, 6-carboxy-2',4',7',4,7-hexachlorofluorescein (HEX), 6-carboxy- 4',5'-dichloro-2',7'-dimethoxy fluorescein (JOE), N,N,N',N'-tetramethyl-6-carboxyrhodamine (TAMRA), 6-carboxy-X-rhodamine (ROX), 5-carboxyrhodamine-6G (R6G5), 6-carboxyrhodamine-6G (RG6), rhodamine 110; Cy3, Cy5, Cy7, coumarins, such as umbelliferone, benzimides, such as Hoechst 33258; phenanthridines, such as Texas Red, ethidium bromides, acridine dyes, carbazole dyes, phenoxazine dyes, porphyrin dyes, polymethine dyes, cyanine dyes, such as Cy3, Cy5, BODIPY dyes, quinoline dyes and Alexa dyes. Other labels, such as the insertion of biotin or one or more haptens, such as, e.g., digoxigenin, which allow a direct or indirect detection of the nucleic acid. Indirect detection, such as, e.g., via antibodies, which in turn, e.g., enzymatic detection via an enzyme coupled to an antibody. Also, via the introduction of nanoparticles, which are coupled to, e.g., antibodies or an affinity ligand, an indirect detection is possible.

The reaction mixture according to the invention in each case comprises a deoxyribonucleotide at a concentration of 0.01 mmol to 10 mmol. The individual deoxyribonucleotide A, C, G and T is preferably present at a concentration of 0.2 mmol to 2 mmol in each case. It is especially preferred if the deoxyribonucleotides A, C, G and T are present together. Each individual one is present in this preferred embodiment at a concentration of 0.5 mmol.

In addition, the reaction mixture according to the invention comprises a buffer. This buffer has a pH of 6 to 10. In addition, in the reaction mixture according to the invention, $Mg^{2+}$ ions are found. In an especially preferred embodiment, the reaction mixture according to the invention has a buffer with a pH of 6.8 to 9. The reaction mixture can further comprise additional ions, which can be selected from the group that comprises $Mn^{2+}$, $K^+$, $NH^{4+}$, and $Na^+$. The presence of two different enzyme activities is essential for the reaction mixture according to the invention. The reaction mixture according to the invention comprises at least a first enzyme activity with polyadenylation activity and secondly, a second enzyme activity with reverse transcriptase activity. The preferred embodiments of these activities were already described above for the process. In addition, like the process above, the reaction mixture can comprise additional substances, such as, for example, a volume excluder, a single-strand binding protein, DTT, or one or more competitor-nucleic acids.

If a volume excluder is used, it is preferred that the latter be selected from the group that comprises dextran and polyethylene glycol. Other volume excluders according to this invention are found in EP1411133A1.

If the reaction mixture optionally comprises a competitor-nucleic acid, the latter is selected from the group that comprises homopolymer ribonucleic acids and polyadenoribonucleic acid. Other competitor-nucleic acids according to the invention are disclosed in U.S. Pat. No. 6,300,069.

The reaction mixture according to the invention preferably comprises additional poly-(C)-polynucleotides. The reaction mixture according to the invention especially preferably comprises additional poly-(C)-polyribonucleotides. 1 ng to 300 ng of poly-(C)-polyribonucleotides is preferably incorporated for each 20 μl, 10 ng to 150 ng of poly-(C)-polyribonucleotides is preferably incorporated for each 20 μl of reaction, 25 ng to 100 ng of poly-(C)-polyribonucleotides is especially preferably incorporated for each reaction, and 50 ng to 75 ng of poly-(C)-polyribonucleotides is most preferably incorporated for each 20 μl of reaction.

In addition, the invention relates to a kit, comprising a reaction mixture, as it was described above. The reaction mixture is present in a preferred embodiment in a single reaction vessel. In another embodiment, the kit comprises a reaction vessel, comprising the enzyme with polyadenylation activity, the enzyme with reverse transcriptase activity, optionally the deoxyribonucleotides, optionally at least one ribonucleotide, optionally a buffer containing $Mg^{2+}$, and optionally one or more oligodeoxyribonucleotides in terms of the invention. Optionally, the reaction vessel in the kit according to the invention can contain additional components, as they were indicated for the reaction mixture according to the invention. In addition, the kit can comprise a probe for the 5'-tail of the anchor oligonucleotide according to the invention. In addition, the kit can contain one or more additional deoxyribonucleotides, thus, e.g., a generic primer for detecting the tail sequence that is introduced by reverse transcription. The reaction mixture can be present in "pellet form," thus, e.g., freeze-dried. Additional preparation processes, which do not contain, e.g., liquid forms, are known to one skilled in the art.

In addition, the kit can optionally be combined with reagents as they are necessary for the PCR reaction or real-time PCR reaction. These reagents are preferred for at least one PCR reaction, which allows the detection of at least one of the cDNAs generated in the process according to the invention.

In addition, the kit can comprise optional random primers as well as optionally one or more primers or primer/probes to detect additional target genes in singleplex or multiplex PCR reactions and/or real-time singleplex or multiplex PCR reactions.

The reaction mixture, the process according to the invention or the kit can contain additional target-specific primers. The length of the target-specific primer should be selected such that a specific detection in a PCR reaction is possible; the sequence of the target primer should be specific, such that a binding to only one spot in the generated cDNA sequence is possible. Normally, such a primer has a length of 15 to 30 nucleotides, preferably 17 to 25 nucleotides.

In an especially preferred embodiment, the reaction mixture comprises the enzyme with polyadenylation activity and the enzyme with reverse transcriptase activity as a two-enzyme pre-mix. In this especially preferred embodiment, the kit comprises the two-enzyme-premix-reaction mixture in a reaction vessel and in a separate vessel, a buffer, $Mg^{2+}$, rNTP(s), dNTP(s), optionally one anchor oligonucleotide according to the invention, and optionally random primers, as well as, in addition, optionally a volume excluding reagent and/or a competitor-nucleic acid.

The process according to the invention can, as already explained above, take place in one or more temperature steps. In a preferred embodiment, the process according to the invention takes place in a single temperature step for the incubation and another temperature step for the inactivation of the enzyme. Thus, in a preferred embodiment of the incubation step in which the enzyme activity develops, it is about 37° C. The incubation time is approximately 1 to 120 minutes, preferably 5 to 90 minutes, more preferably 10 to 75 minutes, still more preferably 15 to 60 minutes, still more preferably 20 to 60 minutes to most preferably 50 to 70 minutes. Normally, excessive incubation time is not harmful. In another step that uses the denaturation of the enzymes, a temperature of at least 65° C. but at most 100° C. is used. Preferably, a temperature of about 80-95° C. is used. The denaturation takes place for a period of at least 1 minute, but for at most 30 minutes. In a preferred embodiment, it is denatured for a period of 5 minutes.

The process according to the invention for generating cDNA can subsequently comprise a polymerase chain reaction. If this is the case, a primer that is specific to the tail that is introduced during cDNA synthesis and/or a specific primer is preferably added to the reaction mixture according to the invention. The reaction mixture then also contains a thermostable DNA-polymerase in addition.

The PCR reaction that subsequently takes place can also be a quantitative PCR reaction. It can take place in an array, take place in a microfluid system, take place in a capillary or else be a real-time PCR. Other variants of the PCR are known to one skilled in the art and are equally comprised by the process according to the invention.

The invention also relates to a process for reverse transcription of RNA in DNA, whereby the process comprises the following steps: preparation of a sample that comprises RNA, addition of a first enzyme with reverse transcriptase activity, a buffer, at least one deoxyribonucleotide, an oligonucleotide, incubation of the agents in one or more temperature steps, which are selected such that the enzyme shows activity, whereby the reaction comprises additional poly-(C)-polynucleotides.

Preferably, the enzyme with reverse transcriptase activity is HIV Reverse Transcriptase, M-MLV Reverse Transcriptase, EAIV Reverse Transcriptase, AMV Reverse Transcriptase, *Therms thermophilus* DNA Polymerase I, M-MLV RNAse $H^-$ Superscript, Superscript II, Superscript III, Monsterscript (Epicenter), Omniscript Reverse Transcriptase (Qiagen), Sensiscript Reverse Transcriptase (Qiagen), ThermoScript, Thermo-X (both Invitrogen) or a mixture of two or more enzymes with reverse transcriptase activity and poly-(A)-polymerase from *Escherichia coli*. Especially preferred is HIV Reverse Transcriptase.

The reaction preferably comprises poly-(C)-polyribonucleotides. 1 ng to 300 ng of poly-(C)-polyribonucleotides is incorporated for each 20 µl, preferably 10 ng to 150 ng of poly-(C)-polyribonucleotides is incorporated for each 20 µl of reaction, especially preferably 25 ng to 100 ng of poly-(C)-polyribonucleotides is incorporated for each reaction, and most preferably, 50 ng to 75 ng of poly-(C)-polyribonucleotides is incorporated for each 20 µl of reaction.

In a preferred embodiment of the invention, the sample is a ribonucleic acid that is selected from the group that comprises prokaryotic ribonucleic acids, eukaryotic ribonucleic acids, viral ribonucleic acids, ribonucleic acids whose origin is an archae organism, microribonucleic acids (miRNA), small nucleolar ribonucleic acids (snoRNA), messenger ribonucleic acid (mRNA), transfer-ribonucleic acids (tRNA), non-polyadenylated ribonucleic acids in general, as well as ribosomal ribonucleic acids (rRNA), and moreover, a mixture of two or more of the above-mentioned ribonucleic acids. In the sample, of course, poly-A RNA can also already be contained.

As a template, an RNA can be used that is selected from the group that comprises eukaryotic ribonucleic acids, mRNA, prokaryotic ribonucleic acids, miRNA, snoRNA and rRNA. In the most preferred embodiment of this invention, the sample comprises a ribonucleic acid that is selected from the group that comprises miRNA and snoRNA. Additional mixed samples from varying amounts of ribonucleic acids of varying types accompanied by other substances are preferred.

Based on these advantages of the process according to the invention, the inventor could show that it is possible to prepare and to identify miRNAs efficiently and without contamination. Small amounts of RNA in general can be readily reverse transcribed with the process.

The invention also relates to a kit for reverse transcription that comprises an enzyme with reverse transcriptase activity and poly-(C)-polynucleotides, preferably poly-(C)-polyribonucleotides.

In one embodiment, the RNA is first polyadenylated before the sample is reverse transcribed.

EXAMPLES

Example 1

Demonstration of the feasibility of a coupled, one-stage process of a poly-A-reaction and reverse transcription in the same reaction vessel; effect of various buffers on the efficiency of the detection of a 22-mer RNA oligonucleotide In this experiment, the feasibility of a coupled, one-stage process of a poly-(A)-polymerase reaction and reverse transcription in the same reaction vessel should be demonstrated. For this purpose, the coupled one-stage process was performed under various conditions. This was, on the one hand, the buffer supplied with the poly-(A)-polymerase, and, on the other hand, the buffer supplied with the reverse transcriptase. In addition, a mixture of poly-(A)-polymerase and reverse transcriptase buffers was tested. As a control, the reaction was performed in a two-stage process in a way similar to FIG. 1A.

The reactions were put together as indicated in Table 1.

TABLE 1

Poly-A-Reaction and Reverse Transcription

| | Batch 1 | Batch 2 | Batch 3 | Batch 4 | |
|---|---|---|---|---|---|
| | a/b | a/b | a/b | a/b | |
| | Data from the Final Concentrations | | | Two-Stage Process | |
| Reagents | PAP Buffer | RT Buffer | Mixture of the Two Buffers | 1.) PAP Reaction | 2.) RT Reaction |
| 5x PAP Buffer | 1x | | 1x | 1x | |
| 10x RT Buffer | | 1x | 1x | | 1x |
| $MnCl_2$, 25 mmol Solution | 2.5 mmol | | 2.5 mmol | 2.5 mmol | |
| rATP, 10 mmol | 1 mmol | 1 mmol | 1 mmol | 1 mmol | |
| Poly-(A)-polymerase, 2 U/µl | 4 U (0.2 U/µl) | 2 U (0.1 U/µl) | 4 U (0.2 U/µl) | 2 U (0.2 U/µl) | |
| dNTP Mix (dA, dT, dG, dC, 5 mmol each) | 0.5 mmol | 0.5 mmol | 0.5 mmol | | 0.5 mmol |
| UniGAPdT Primer, 10 µmol | 1 µmol | 1 µmol | 1 µmol | | 1 µmol |
| RNase Inhibitor, 10 U/µl | 10 U | 10 U | 10 U | | 10 U |

TABLE 1-continued

| Poly-A-Reaction and Reverse Transcription | | | | | |
|---|---|---|---|---|---|
| | Batch 1 | Batch 2 | Batch 3 | Batch 4 | |
| | a/b | a/b | a/b | a/b | |
| | Data from the Final Concentrations | | | Two-Stage Process | |
| Sensiscript Reverse Transcriptase | 1 µl | 1 µl | 1 µl | | 1 µl |
| RNase-Free Water | Variable | Variable | Variable | Variable | Variable |
| a) mleu7a | 2 × 10E9 Copies | 2 × 10E9 Copies | 2 × 10E9 Copies | 2 × 10E9 Copies | 10 µl of PAP Reaction 1.) |
| b) Neg Control ($H_2O$ instead of mleu7a) | $H_2O$ | $H_2O$ | $H_2O$ | $H_2O$ | |
| a) Corn RNA | 50 ng | 50 ng | 50 ng | 50 ng | |
| b) Neg Control ($H_2O$ instead of Corn RNA) | $H_2O$ | $H_2O$ | $H_2O$ | $H_2O$ | |
| Total Volume | 20 µl | 20 µl | 20 µl | 10 µl | 20 µl |
| Incubation | 1 Hour, 37° C. 5 Minutes, 93° C. | | 1 Hour 37° C., Then Another Hour at 2.) RT Reaction | 1 Hour, 37° C. 5 Minutes, 93° C. | |

PAP: Poly A Polymerase
RT: Reverse Transcription
rATP: Adenosine 5'-Triphosphate For this purpose, the reagents indicated in Table 2 were used.

TABLE 2

| Materials for the Poly-A-Reaction and Reverse Transcription | |
|---|---|
| Poly-(A)-Polymerase | Ambion; Material Number 80 U: 2030 |
| Sensiscript RT Kit | Qiagen; Material Number 50rxn: 205211 |
| Adenosine 5'-Triphosphate (rATP) | Amersham; Material Number 25 µmol: 27-2056-01 |
| RNase Inhibitor | Promega; Material Number: N2511 |
| Uni GAP dT Primer | 5'-TGG AAC GAG ACG ACG ACA GAC CAA GCT TCC CGT TCT CAG CCT TTT TTT TTT TTT TTT TTT TTV VN-3' (SEQ ID NO: 2) |
| Corn RNA | From 1 g of Ground Corn Husks with Qiagen RNeasy Mini Kit (Cat. No. 74106); Plant Protocol with 10x Upscale (Maxi Shredder and Column) |
| mleu7a RNA Oligonucleotide | 5'-UGA GGU AGU AGG UUG UAU AGU U-3' (SEQ ID NO: 1) |

In each case, reactions were conducted with templates (1a, 2a, 3a, 4a, all with a synthetic RNA oligonucleotide in a background of corn RNA) or without templates (1b, 2b, 3b, 4b, all were added to $H_2O$ instead of templates). The reactions without templates were conducted as controls for the possible occurrence of nonspecific background. Corn RNA was selected as background RNA since the sequence of the 22-mer RNA oligonucleotide to be detected does not occur in corn.

After the inactivation of the enzymes (see Table: 5 minutes at 93° C.), 2 µl each of the batches 1a/b to 4a/b was used as templates in a real-time PCR. The preparation of the real-time PCR was carried out in three-fold batches as indicated in Table 3 with QuantiTect SYBR Green PCR Kit (Catalog No. 204143) and the primers indicated in Table 4.

TABLE 3

| Components for SYBR Green Real-Time PCR | |
|---|---|
| | Final Concentration |
| 2x SYBR Green PCR Master Mix | 1x |
| Hum Uni Primer, 10 µmol | 0.5 µmol |
| miRNA Primer let7/short, 10 µmol | 0.5 µmol |
| RNase-Free Water | Variable |
| PAP-/RT-Reaction | 2 µl |
| Final Reaction Volume | 20 µl |

TABLE 4

| Materials for the SYBR Green PCR (Table 4 discloses SEQ ID NOS 4 and 3, respectively, in order of appearance) | |
|---|---|
| QuantiTect SYBR Green PCR Kit (200) | Qiagen; Material Number: 204143 |
| let 7short (Specific miRNA Primer) | 5'-GAG GTA GTA GGT TGT ATA G-3' |
| Hum Uni Primer | 5'-AAC GAG ACG ACG ACA GAC-3' |

The sequence 5'-AAC GAG ACG ACG ACA GAC-3' (SEQ ID NO: 3) that is contained in the universal tall-primer Hum Uni Primer was described in US2003/0186288A1.

The PCR protocol consisted of an initial reactivation of the HotStarTaq polymerase that is contained in the QuantiTect SYBR Green PCR Master Mix for 15 minutes at 95° C., followed by 40 cycles for 15 seconds at 94° C., 30 seconds at 52° C., and 30 seconds at 72° C. (see Table 5).

TABLE 5

| PCR Protocol for SYBR Green Real-Time PCR | | |
|---|---|---|
| PCR Initial Reactivation | 15 Minutes, 95° C. | |
| Denaturation | 15 Seconds, 94° C. | 40x |
| Annealing | 30 Seconds, 52° C. | |

TABLE 5-continued

| PCR Protocol for SYBR Green Real-Time PCR | |
|---|---|
| Extension (Data Acquisition) | 30 Seconds, 72° C. |
| Melt Curve | |

The acquisition of the fluorescence data was carried out during the 72° C. extension step. The PCR analyses were performed with an ABI PRISM 7700 (Applied Biosystems) in a reaction volume of 20 µl.

The PCR products were then subjected to a melt curve analysis. The latter was performed on an ABI PRISM 7000 real-time PCR instrument.

TABLE 6

Results of a Real-Time PCR Analysis of the Batches from Table 1

| Detector | PAP/RT | Template | Ct | Ct Agent | CV in % |
|---|---|---|---|---|---|
| SYBR | 1) PAP Buffer | a) mleu7a | 25.64 | | |
| Green | | 2 × 10^8 Copies + | 25.22 | 25.50 | 0.95 |
| | | Corn cDNA, 5 ng | 25.64 | | |
| | | b) $H_2O$ in PAP - | No Ct | | |
| | | RT Reaction | No Ct | No Ct | |
| | | | No Ct | | |
| | 2) RT Buffer | a) mleu7a | 17.43 | | |
| | | 2 × 10^8 Copies + | 17.31 | 17.32 | 0.58 |
| | | Corn cDNA, 5 ng | 17.23 | | |
| | | b) $H_2O$ in PAP- | No Ct | | |
| | | RT Reaction | No Ct | No Ct | |
| | | | No Ct | | |
| | 3) Mixture of | a) mleu7a | 30.41 | | |
| | Both Buffers | 2 × 10^8 Copies + | 30.23 | 30.28 | 0.36 |
| | | Corn cDNA, 5 ng | 30.21 | | |
| | | b) $H_2O$ in PAP- | No Ct | | |
| | | RT Reaction | No Ct | No Ct | |
| | | | No Ct | | |
| | 4) Two-Stage | a) mleu7a | 25.54 | | |
| | Process | 2 × 10^8 Copies + | 25.74 | 25.64 | 0.39 |
| | | Corn DNA, 5 ng | 25.65 | | |
| | | b) $H_2O$ in PAP- | No Ct | | |
| | | RT Reaction | No Ct | No Ct | |
| | | | No Ct | | |

The identity of the PCR products was then examined with the aid of agarose-gel electrophoresis. For this purpose, 10 µl of each PCR reaction was loaded onto a 2% agarose gel colored with ethidium bromide and separated. 100 bp Lader (Invitrogen, Catalog No. 15628-050) was used as a size standard. The results are depicted in FIG. 3.

Example 2

Demonstration of the reproducibility and specificity of a coupled one-stage process of poly-(A)-polymerase reaction and reverse transcription in the same reaction vessel In this experiment, the feasibility of a coupled one-stage process of poly-(A)-polymerase reaction and reverse transcription should be reproduced in the same reaction vessel. For this purpose, the efficiency of the one-stage process of the poly-(A)-polymerase reaction and reverse transcription in the same reaction vessel was analyzed in the example of the detection of a 22-mer RNA oligonucleotide. A reverse transcription reaction for the template that is used according to standard conditions was used as a control for the specificity of the detection.

For this purpose, the coupled one-stage process was performed under various conditions. The latter were, on the one hand, the buffer supplied with poly-(A)-polymerase, and, on the other hand, the buffer supplied with the reverse transcriptase (Tables 7, 8).

TABLE 7

Designation and Components of the Reactions Conducted

| Designation | Buffer | Template |
|---|---|---|
| Reaction 1 | 1-Step Process | RNA 50 ng + mleu7a 2 × 10E9 Copies |
| Reaction 2 | in PAP Buffer | RNA, 50 ng |
| Reaction 3 | | Negative Control: $H_2O$ |
| Reaction 4 | 1-Step Process | RNA 50 ng + mleu7a 2 × 10E9 Copies |
| Reaction 5 | in RT Buffer | RNA, 50 ng |
| Reaction 6 | | Negative Control: $H_2O$ |
| Reaction 7 | Standard RT | RNa 50 ng + mleu7a 2 × 10E9 Copies |
| Reaction 8 | | RNA, 50 ng |

TABLE 8

Composition of the Combined Poly-(A)-Polymerase/Reverse Transcription Reaction and the Standard Reverse Transcription Reaction

| | Data from the Final Concentrations | | |
|---|---|---|---|
| Reagents | Reactions 1, 2, 3 PAP Buffer | Reactions 4, 5, 6 RT Buffer | Reactions 7, 8 Standard RT |
| 5x PAP Buffer | 1x | | |
| 10x RT Buffer | | 1x | 1x |
| $MnCl_2$, 25 mmol | 2.5 mmol | | |
| rATP, 10 mmol | 1 mmol | 1 mmol | |
| Poly-(A)-Polymerase, 2 U/µl | 2 U (0.1 U/µl) | 2 U (0.1 U/µl) | |
| dNTP Mix (dA, dT, dG, dC, 5 mmol each) | 0.5 mmol | 0.5 mmol | 0.5 mmol |
| UniGAPdT Primer, 10 µmol | 1 µmol | 1 µmol | 1 µmol |
| RNase Inhibitor, 10 U/µl | 10 U | 10 U | 10 U |
| Sensiscript Reverse Transcriptase | 1 µl | 1 µl | 1 µl |
| RNase-Free Water | Variable | Variable | Variable |
| mleu7a; Reactions 1, 4, 7 | 2 × 10E9 Copies | 2 × 10E9 Copies | 2 × 10E9 Copies |
| RNA: Reactions 1, 2, 4, 5, 7, 8 | 50 ng | 50 ng | 50 ng |
| Neg. Control ($H_2O$ instead of RNA) in Reactions 3, 6 | $H_2O$ | $H_2O$ | |
| Total Volume | 20 µl | 20 µl | 20 µl |
| Incubation | | 1 Hour, 37° C. 5 Minutes, 93° C. | |

All reaction batches were then divided:

Batches a) 10 µl was removed and stored at 4° C.;

For all batches b): Uni GAP dT primer [1 µmol] and 0.5 µl of Sensiscript Reverse Transcriptase were added again to 10 µl, and a reverse transcription was performed again (for 1 hour at 37° C.), then the reverse transcriptase was inactivated (5 minutes, 93° C.).

In addition, a standard reverse transcription reaction was performed with the purpose of examining the specificity of the detection in the subsequent PCR (Tables 7, 8, see above). After the poly-(A)-polymerase reaction and reverse transcription, the samples were divided. In each case, Uni Gap dT primer and reverse transcriptase were added again to half of a sample (see Table 7, above). The purpose here was to rule out the possibility that false-positive signals are produced to a small extent by an undesired adherence of an A-Tail to the Uni Gap dT primer. As a template, total-RNA was added, which was isolated from human blood with an RNeasy Midi Kit (QIAGEN, Hilden, Germany, Cat. No. 75144).

The components that are used in the individual reactions and their designations are put together in Table 7, see above. The detected 22-mer RNA corresponds in the sequence thereof to the human leu7a miRNA (EMBL Acc#: AJ421724) and may be expressed in human blood cells such as leukocytes. However, such small RNAs are only very inefficiently purified because of the purification technology of the RNeasy process that is used for the RNA isolation. The RNeasy process ensures only an efficient binding of RNAs with a size above 200 bases on the silica membrane of the RNeasy column (QIAGEN RNeasy Midi/Maxi Handbook, 06/2001, p. 9), and thus small RNAs such as miRNAs are stripped out to a large extent.

In addition, the synthetic 22-mer RNA was used at a concentration that is clearly higher than the endogenic copy number expected. The reactions were put together as indicated in Table 8 (see above).

To this end, the reagents indicated in Table 9 were used.

TABLE 9

| Materials for the Poly-A-Reaction and Reverse Transcription | |
|---|---|
| Poly (A) Polymerase | Ambion; Material Number 80 U: 2030 |
| Sensiscript RT Kit | Qiagen; Material Number 50rxn: 205211 |
| Adenosine 5'-Triphosphate (rATP) | Amersham; Material Number 25 µmol: 27-2056-01 |
| RNase Inhibitor | Promega; Material Number: N2511 |
| Uni GAP dT Primer | 5'-TGG AAC GAG ACG ACG ACA GAC CAA GCT TCC CGT TCT CAG CCT TTT TTT TTT TTT TTT TTT TTV VN-3' (SEQ ID NO: 2) |
| RNA | RNA Leukocytes from Human Blood Isolated with an RNeasy Midi Kit (QIAGEN, Cat. No. 75144) |
| mleu7a RNA Oligonucleotide | 5'-UGA GGU AGU AGG UUG UAU AGU U-3' (SEQ ID NO: 1) |

After the inactivation of the enzymes (5 minutes at 93° C.), the batches were diluted 1:2 with water, and 2 µl each of the batches 1a/b to 8a/b was used as a template in a real-time SYBR Green PCR. The preparation of the real-time PCR was carried out in two-fold batches as indicated in Table 9 (above) with QuantiTect SYBR Green PCR Kit (Catalog No. 204143) and the primers indicated in Table 10.

TABLE 10

| Components for SYBR Green Real-Time PCR | Final Concentration |
|---|---|
| 2x SYBR Green PCR Master Mix | 1x |
| Hum Uni Primer, 10 µmol | 0.5 µmol |
| miRNA Primer let 7short, 10, µmol | 0.5 µmol |
| RNase-Free Water | Variable |
| PAP-/RT-Reaction 1:2 prediluted | 2 µl |
| Final Reaction Volume | 20 µl |

The sequence 5'-AAC GAG ACG ACG ACA GAC-3' (SEQ ID NO: 3) contained in the universal tail-primer Hum Uni Primer was described in US 2003/0186288A1. The PCR protocol consisted of an initial reactivation of the HotStarTaq Polymerase contained in the QuantiTect SYBR Green PCR Master Mix for 15 minutes at 95° C., followed by 40 cycles for 15 seconds at 94° C., 30 seconds at 52° C. and 30 seconds at 72° C. (see Table 11).

TABLE 11

| Materials for the SYBR Green PCR (Table 11 discloses SEQ ID NOS 4 and 3, respectively, in order of appearance) | |
|---|---|
| QuantiTect SYBR Green PCR Kit (200) | Qiagen; Material Number: 204143 |
| let 7short (Specific miRNA Primer) | 5'-GAG GTA GTA GGT TGT ATG G-3' |
| Hum Uni Primer | 5'-AAC GAG ACG ACG ACA GAC-3' |

The acquisition of the fluorescence data was carried out during the 72° C. extension step. The PCR analyses were performed with an Applied Biosystems 7500 Fast Real-Time PCR System (Applied Biosystems) in a reaction volume of 20 µl and then a melt curve analysis was performed.

The coupled one-stage poly-(A)-reaction and reverse transcription are possible both in poly-(A)-polymerase buffer and in RT buffer, which is evident based on real-time PCR analyses. Preferred buffer conditions were already indicated in the text (see above). They show large differences in the Ct values that are obtained when using the different buffers.

The standard reverse transcription reactions (reactions 3, 6), performed for the monitoring of the specificity, are all negative (no Ct) without poly-(A)-reactions. This allows the conclusion that without polyadenylation of the 22-mer RNA (1, 4, 7) or the naturally occurring miRNA (2, 5, 8) as expected, no template for a PCR amplification is present and therefore no signal can be generated ("no Ct").

In the "RT doubled" batches, additional RT enzymes and Uni Gap dT Primer were added after the first incubation with the purpose of making poly-(A)-tailed UniGap dT Primer detectable by an RT reaction, possibly in the first reaction. All of these batches showed no Ct, i.e., undesirable artifacts are not detectable.

Undesirable artifacts such as poly-(A)-tailing of the primer used for the cDNA synthesis are also not detectable.

Example 3

Detection of various miRNAs using the process according to the invention.

In this experiment, it should be demonstrated that several targets can be detected by miRNA-specific PCR Primers from a cDNA template that was synthesized with the process according to the invention with poly-(A)-reactions of common reverse transcription. For this purpose, a process was performed with 293 RNA as a template. A reverse transcription reaction for the template that is used according to standard conditions was used as a control for the specificity of the detection.

In the subsequent SYBR Green PCR, overall in each case one of 4 different specific primers for miRNAs together with the tail of specific primers was used. In addition, a primer located on the 3'-end of the human β-actin transcript was used together with a tail-specific primer to examine the efficiency of the poly-A-reaction and reverse transcription.

For the poly-A-reaction and reverse transcription (PAP+RT reaction), the reagents from Table 13 were pipetted together as indicated in Table 16.

TABLE 13

| Materials for the Poly A Reaction and Reverse Transcription (Table 13 discloses SEQ ID NO: 2) | |
|---|---|
| Poly (A) Polymerase | Ambion; Material Number 80 U: 2030 |
| Sensiscript RT Kit | Qiagen; Material Number 50rxn: 205211 |
| Adenosine 5'-Triphosphate (rATP) | Amersham; Material Number 25 μmol: 27-2056-01 |
| RNase Inhibitor | Promega; Material Number: N2511 |
| Uni GAP dT Primer | 5'-TGG AAC GAG ACG ACG ACA GAC CAA GCT TCC CGT TCT CAG CCT TTT TTT TTT TTT TTT TTT TTV VN-3' |
| 293 RNA: From Human Cell Line 293 (ATCC Number: CRL-1573) | With Qiagen RNeasy Midi Kit Isolated |

TABLE 16

| PAP + RT Reaction | |
|---|---|
| Reagents | Final Concentration |
| 10x Buffer RT | 1x |
| rATP, 10 mmol | 1 mmol |
| Poly A Polymerase 2 U/μl | 2 U |
| dNTP Mix (ATGC, 5 mmol each) | 0.5 mmol |
| Uni GAP dT Primer, 10 μmol | 1 μmol |
| RNase Inhibitor, 10 U/μl | 10 U |
| Sensiscript Reverse Transcriptase | 1 μl |
| RNase-Free Water | Variable |
| a) 293 RNA, 20 ng/μl | 5 μl (100 ng) |
| b) $H_2O$ for Neg Control | 5 μl |
| Total Volume | 20 μl |
| Incubation | 1 Hour, 37° C.<br>5 Minutes, 93° C. |

In reaction a), 293 RNA was added as a negative control (neg control) and in reaction b), water was added as a negative control. As a control for the specificity of the detection, a standard reverse transcription reaction with the reagents indicated in Table 14 was prepared based on the diagram in Table 17.

TABLE 14

| Materials for Reverse Transcription (Table 14 discloses SEQ ID NO: 2) | |
|---|---|
| Sensiscript RT Kit | Qiagen; Material Number 50rxn: 205211 |
| RNase Inhibitor | Promega; Material Number: N2511 |
| Uni GAP dT Primer | 5'-TGG AAC GAG ACG ACG ACA GAC CAA GCT TCC CGT TCT CAG CCT TTT TTT TTT TTT TTT TTT TTV VN-3' |
| 293 RNA | With Qiagen RNeasy Midi Kit Isolated |

TABLE 17

| Standard RT Reaction | |
|---|---|
| Reagents | 2.) RT Reaction |
| 10x Buffer RT | 1x |
| dNTP Mix (ATGC, 5 mmol each) | 0.5 mmol |
| Uni GAP dT Primer, 10 μmol | 1 μmol |
| RNase Inhibitor, 10 U/μl | 10 U |
| Sensiscript Reverse Transcriptase | 1 μl |
| RNase-Free Water | Variable |
| c) 293 RNA, 20 ng/μl | 5 μl (100 ng) |
| d) $H_2O$ for Neg Control | 5 μl |
| Total Volume | 20 μl |
| Incubation | 1 Hour, 37° C.<br>5 Minutes, 93° C. |

In reaction c), 293 RNA was added as negative control (neg control), and in reaction d), water was added as negative control. The samples were then incubated for one hour at 37° C. To stop the reaction, the reactions were incubated for 5 minutes at 93° C.; the enzymes are inactivated by this temperature step.

After the inactivation of the enzymes, the batches 1:2 were diluted with water and 2 μl each of the batches a) to d) were used as templates in a real-time SYBR Green PCR. The materials for the PCR are indicated in Table 15.

TABLE 15

| Materials for the SYBR Green PCR (Table 15 discloses SEQ ID NOS 4-8 and 3, respectively, in order of appearance) | |
|---|---|
| QuantiTect SYBR Green PCR Kit (200) | Qiagen; Material Number: 204143 |
| let 7short (Specific miRNA Primer) | 5'-GAG GTA GTA GGT TGT ATA G-3' |
| hsa-miR-24 (Specific miRNA Primer) | 5'-TGG CTC AGT TCA GCA GGA-3' |
| hsa-miR-15a (Specific miRNA Primer) | 5'-TAG CAG CAC ATA ATG GTT T-3' |
| hsa-miR-16 (Specific miRNA Primer) | 5'-TAG CAG CAC GTA AAT ATT G-3' |
| β-Actin 3' Primer | 5'-GTA CAC TGA CTT GAG ACC AGT TGA ATA AA-3' |
| Hum Uni Primer | 5'-AAC GAG ACG ACG ACA GAC-3' |

Ten different reaction batches were pipetted. In reactions 1-5 (Table 18), in each case the miRNA-specific or β-actin 3' primer and the tail primer (Hum Uni) were used.

TABLE 18

| SYBR GREEN PCR Reactions 1-5 | |
|---|---|
| Components for SYBR Green PCR | Final Concentration |
| 2x SYBR Green PCR Master Mix | 1x |
| Hum Uni Primer, 10 μmol | 0.5 μmol |
| One Specific miRNA Primer Each (10 μmol) | 0.5 μmol |
| let 7short | |
| hsa-miR-24 | |
| hsa-miR-15a | |
| hsa-miR-16 | |
| or β-Actin 3' Primer | |
| RNase-Free Water | Variable |
| PAP + RT Reaction a) b) 1:2 prediluted | 2 μl (5 ng) |
| Standard RT Reaction c) d) 1:2 prediluted | 2 μl (5 ng) |
| or $H_2O$ as Neg Control | 2 μl |
| Final Reaction Volume | 20 μl |

In reactions 6-10 (Table 19), in each case only one primer was used, either the miRNA specific primer or the tail-specific primer.

In reactions 6-10 (Table 19), in each case only one primer was used, either the miRNA specific primer or the tail-specific primer.

TABLE 19

| Control with Only One Primer Reaction 6-10 | |
|---|---|
| Components for SYBR Green PCR | Final Concentration |
| 2x SYBR Green PCR Master Mix | 1x |
| One Specific miRNA Primer Each (10 μmol) | 0.5 μmol |
| let 7short | |
| hsa-miR-24 | |
| hsa-miR-15a | |
| hsa-miR-16 | |
| Each with 3' Hum Uni Primer | |
| RNase-Free Water | Variable |
| PAP + RT Reaction a) b) 1:2 Prediluted | 2 μl (5 ng) |
| Standard RT Reaction c) d) 1:2 Prediluted | 2 μl (5 ng) |
| or $H_2O$ as Neg Control | 2 μl |
| Final Reaction Volume | 20 μl |

The sequence in which the primers were used in the reactions can be seen from Table 20. The preparation of the real-time PCR was carried out in two-fold batches.

TABLE 20

| Primer | |
|---|---|
| | Primer |
| Reaction 1 | β-Actin 3'Primer + Hum Uni |
| Reaction 2 | let 7short + Hum Uni |
| Reaction 3 | hsa-miR-24 + Hum Uni |
| Reaction 4 | hsa-miR-15[a] + Hum Uni |
| Reaction 5 | hsa-miR-16 + Hum Uni |
| Reaction 6 | Hum Uni |
| Reaction 7 | let 7short |
| Reaction 8 | hsa-miR-24 |
| Reaction 9 | hsa-miR-15a |
| Reaction 10 | hsa-miR-16 |

The sequence AAC GAG ACG ACG ACA GAC (SEQ ID NO: 3) contained in the universal Tail-Primer Hum Uni Primer was described in US2003/0186288A1.

The PCR protocol consisted of an initial reactivation of the HotStarTaq polymerase contained in the QuantiTect SYBR Green PCR Master Mix for 15 minutes at 95° C., followed by 40 cycles for 15 seconds at 94° C., 30 seconds at 52° C., and 30 seconds at 72° C. (see Table 21). The acquisition of the fluorescence data was carried out during the 72° C. extension step. The PCR analyses were performed with an Applied Biosystems 7000 Fast Real-Time PCR System (Applied Biosystems) in a reaction volume of 20 μl, and then a melt curve analysis was performed.

TABLE 21

| 3-Step PCR Protocol | | |
|---|---|---|
| PCR Initial Reactivation | 15 Minutes, 95° C. | |
| Denaturation | 15 Seconds, 94° C. | 40x |
| Annealing | 30 Seconds, 52° C. | |
| Extension | 30 Seconds, 72° C. | |
| Melt Curve | | |

It is shown that the efficiency of the reverse transcription performed under standard conditions and of the process according to the invention for the β-actin system that is selected by way of example is comparable, which is evident in comparable Ct values in the real-time PCR (FIG. 6).

When using the cDNA produced under standard conditions, the real-time PCR yields very high Ct values of above 38, which mean a very good specificity of the detection in a real-time PCR that is performed with SybrGreen (FIG. 6). In the agarose gel analysis of the PCR products, PCR products of the expected values were detected (FIG. 8), or no product was detected when using the cDNA produced under standard conditions.

The miR24 product represents an acquisition. Here, when the cDNA produced under standard conditions is used, a PCR product of the wrong size is produced (FIG. 8, see also FIG. 6). This product cannot be detected, as soon as a cDNA is used, which was produced using the process according to the invention (FIG. 8).

All control reactions in which water instead of RNA template was used in the reverse transcription or the process according to the invention show no signal, i.e., no Ct value in the real-time PCRs in question was obtained (FIG. 7, upper part). The same also applies for reactions in which only one primer was used (FIG. 7, upper part). Also, no Ct value was obtained for negative controls, in which water instead of cDNA was used in the PCR (FIG. 7).

Example 4

Detection of miRNA using the coupled, one-stage process of poly-A-reaction and reverse transcription and subsequent detection of the generated cDNA over real-time pCR with a tail-specific probe In this experiment, a real-time PCR was performed, in which a Taqman probe was used, which has a specific binding site on the tail-primer (Uni Gap dT). The detection via a probe represents a conceivable alternative for the detection via SYBR Green real-time PCR. The use of the probe offers the additional possibility of a multiplex PCR, i.e., a co-amplification or one or more additional target nucleic acids, such as an internal control, which can be, e.g., a housekeeping gene.

For the poly-A-reaction and reverse transcription (PAP+RT reaction), the reagents from Table 22 were pipetted together as indicated in Table 24.

TABLE 22

| Materials for the Poly A Reaction and Reverse Transcription (Table 22 discloses SEQ ID NOS 2 and 1, respectively, in order of appearance) | |
|---|---|
| Poly (A) Polymerase | Ambion; Material Number 80 U: 2030 |
| Sensiscript RT Kit | Qiagen; Material Number 50rxn: 205211 |
| Adenosine 5'-Triphosphate (rATP) | Amersham; Material Number 25 µmol: 27-2056-01 |
| RNase Inhibitor | Promega; Material Number; N2511 |
| Uni GAP dT Primer | 5'-TGG AAC GAG ACG ACG ACA GAC CAA GCT TCC CGT TCT CAG CCT TTT TTT TTT TTT TTT TTT TTV VN-3' |
| mleu7a Oligonucleotide | 5'-UGA GGU AGU AGG UUG UAU AGU U-3' |

TABLE 24

| PAP + RT Reaction | |
|---|---|
| Reagents | Final Concentration |
| 10x Buffer RT | 1x |
| rATP, 10 mmol | 1 mmol |
| Poly A Polymerase, 2 U/µl | 2 U |
| dNTP Mix (ATGC, 5 mmol each) | 0.5 mmol |
| Uni GAP dT Primer, 10 µmol | 1 µmol |
| RNase Inhibitor, 10 U/µl | 10 U |
| Sensiscript Reverse Transcriptase | 1 µl |
| RNase-Free Water | Variable |
| mleu7 (10^9 Copies/µl) | 2 µl (2 × 10^9 Copies) |
| Total Volume | 20 µl |
| Incubation | 1 Hour, 37° C. 5 Minutes, 93° C. |

Then, the reaction batch was incubated at 37° C., followed by an inactivation of the enzymes for 5 minutes to 93° C.

After the inactivation of the enzymes, 2 µl of the undiluted batch was used as a template in a real-time PCR, which contained a Taqman probe for detection. The materials for the PCR are indicated in Table 23 and were pipetted together as indicated in Table 25.

TABLE 23

| Materials for the QT Probe PCR (Table 23 discloses SEQ ID NOS 4, 3 and 9, respectively, in order of appearance) | |
|---|---|
| QuantiTect Probe PCR Kit (200) | Qiagen Material No.: 204343 |
| let 7short (Specific miRNA primer) | 5'-GAG GTA GTA GGT TGT ATA G-3' |
| Hum Uni Primer | 5'-AAC GAG ACG ACG ACA GAC-3' |
| Hum Uni Probe | 5'-HEX-CAA GCT TCC CGT TCT CAG CC-BHQ-3' 5' Reporter Dye: HEX 3' Quencher: Black Hole-Quencher 1 |

TABLE 25

| QuantiTect Probe PCR | |
|---|---|
| Components for QuantiTect Probe PCR | Final Concentration |
| 2x QuantiTect Probe PCR Master Mix | 1x |
| Hum Uni Primer, 10 µmol | 0.5 µmol |
| let 7short (specific miRNA Primer) | 0.5 µmol |
| RNase-Free Water | Variable |
| PAP + RT Reaction, Undiluted | 2 µl (2 × 10^8 Copies) |
| Final Reaction Volume | 20 µl |

The batch of real-time PCR was carried out in two-fold batches.

The sequence AAC GAG ACG ACG ACA GAC (SEQ ID NO: 3) contained in the universal tail-primer Hum Uni Primer was described in US2003/0186288A1. The Taqman probe sequence was removed from the human GAPDH gene locus, it is not contained in US2003/0186288A1.

The PCR protocol consisted of an initial reactivation of the HotStarTaq polymerase contained in the QuantiTect Probe PCR Master Mix for 15 minutes at 95° C., followed by 45 cycles for 15 seconds at 94° C. and 30 seconds at 52° C. (see Table 26).

TABLE 26

| 2-Step PCR Protocol | | |
|---|---|---|
| PCR Initial Reactivation | 15 Minutes, 95° C. | |
| Denaturation | 15 Seconds, 94° C. | 45x |
| Annealing | 30 Seconds, 52° C. | |

The acquisition of the fluorescence data was carried out during the 52° C. annealing step. The PCR analyses were performed with a 7700 sequence detection system (Applied Biosystems) in a reaction volume of 20 µl. The PCR results are shown in Table 27.

TABLE 27

| PCR Results | | | |
|---|---|---|---|
| mleu7a | Ct | Ct Agent | CV in % |
| Undiluted, 2 × 10^8 | 20.24 20.37 | 20.31 | 0.45 |

A detection using a tail-specific probe is possible and yields the expected result.

Example 5

Effect of poly-A-polymerase concentration and incubation time in the coupled, one-stage process of poly-A-reaction and reverse transcription.

In this test, two concentrations of poly-A-polymerase (2 U or 0.5 U) were used for 15 minutes or 1 hour respectively in the process according to the invention. All conditions were tested in each case in the RT buffer (Qiagen) and poly-A-polymerase buffer.

For the poly-A-reaction and reverse transcription (PAP+ RT reaction), the reagents from Table 28 were pipetted together as indicated in Table 30: reaction a) 2 U of poly-A-polymerase, reaction b) 0.5 U of poly-A-polymerase).

TABLE 28

| Materials for the Poly A Reaction and Reverse Transcription (Table 28 discloses SEQ ID NOS 2 and 1, respectively, in order of appearance) | |
|---|---|
| Poly (A) Polymerase | Ambion; Material Number 80 U: 2030 |
| Sensiscript RT Kit | Qiagen; Material Number 50rxn: 205211 |
| Adenosine 5'-Triphosphate (rATP) | Amersham; Material Number, 25 µmol: 27-2056-01 |
| RNase Inhibitor | Promega; Material Number: N2511 |
| Uni GAP dT Primer | 5'-TGG AAC GAG ACG ACG ACA GAC CAA GCT TCC CGTTCT CAG CCT TTT TTT TTT TTT TTT TTT TTV VN-3' |
| Corn RNA | From 1 g of Ground Corn Husks with Qiagen RNeasy Mini Kit (Cat. No. 74106) according to Plant Protocol. |
| mleu7a Oligonucleotide | 5'-UGA GGU AGU AGG UUG UAU AGU U-3' |

TABLE 30

PAP + RT Reaction

| Reagents | Final Concentration |
|---|---|
| 10x Buffer RT | 1x |
| rATP, 10 mmol | 1 mmol |
| Poly A Polymerase, 2 U/µl | a) 2 U<br>b) 0.5 U |
| dNTP Mix (ATGC, 5 mmol each) | 0.5 mmol |
| Uni GAP dT Primer, 10 µmol | 1 µmol |
| RNase Inhibitor, 10 U/µl | 10 U |
| Sensiscript Reverse Transcriptase | 1 µl |
| RNase-Free Water | Variable |
| mleu7a 10^9 Copies/µl | 2 µl (2 x 10^9 Copies) |
| Corn RNA, 25 ng/µl | 2 µl (50 ng) |
| Total Volume | 20 µl |
| 1.) Incubation | 1 Hour, 37° C.<br>5 Minutes, 93° C. |
| 2.) Incubation | 15 Minutes, 37° C.<br>5 Minutes, 93° C. |

Then, the samples were incubated at 37° C. (1. 1 hour/2. 15 minutes). Then, the reactions were heated for 5 minutes to 93° C., and thus the enzymes were inactivated.

Then, in each case 2 µl was incorporated undiluted into an SYBR Green PCR for each reaction. The reactions were tested two times apiece. For this purpose, the reagents from Table 29 were pipetted together as indicated in Table 31, and then the PCR was performed as indicated in Table 32.

TABLE 29

| Materials for the SYBR Green PCR (Table 29 discloses SEQ ID NOS 4 and 3, respectively, in order of appearance) | |
|---|---|
| QuantiTect SYBR Green PCR Kit (200) | Qiagen; Material Number: 204143 |
| let 7short (Specific miRNA Primer) | 5'-GAG GTA GTA GGT TGT ATA G-3' |
| Hum Uni Primer | 5'-AAC GAG ACG ACG ACA GAC-3' |

TABLE 31

SYBR GREEN PCR

| Components for SYBR Green PCR | Final Concentration |
|---|---|
| 2x SYBR Green PCR Master Mix | 1x |
| Hum Uni Primer, 10 µmol | 0.5 µmol |
| let 7short (Specific miRNA Primer) | 0.5 µmol |
| RNase-Free Water | Variable |
| PAP + RT Reaction 1a) b)/2a) b) | 2 µl (2 x 10^8 Copies) |
| Final Reaction Volume | 20 µl |

TABLE 32

3-Step PCR Protocol

| | | |
|---|---|---|
| PCR Initial Reactivation | 15 Minutes, 95° C. | |
| Denaturation | 15 Seconds, 94° C. | 45x |
| Annealing | 30 Seconds, 52° C. | |
| Extension | 30 Seconds, 70° C. | |
| Melt Curve | | |

The PCR protocol consisted of an initial reactivation of the HotStarTaq polymerase contained in the QuantiTect SYBR Green PCR Master Mix for 15 minutes at 95° C., followed by 40 cycles for 15 seconds at 94° C., 30 seconds at 52° C., and 30 seconds at 72° C. (see Table 32 above). The acquisition of the fluorescence data was carried out during the 72° C. extension step. The PCR analyses were performed with an Applied Biosystems 7000 Real-Time PCR System (Applied Biosystems) in a reaction volume of 20 µl, and then a melt curve analysis was performed.

A dependency of the efficiency of the one-stage process of the poly-A-reaction and reverse transcription both on the concentration of the poly-A-polymerase and on the incubation time can be seen (see FIG. 9).

Example 6

Implementation of the process according to the invention with various reverse transcriptases.

The process according to the invention was applied with a total of five different reverse transcriptases (see Table 35) in the buffer RT (Qiagen) (reactions 1-5) and additionally, for purposes of comparison, in each case in the buffer supplied with the reverse transcriptase (reactions 6-9).

TABLE 35

Reverse Transcriptases and Buffers that are Used

| | | |
|---|---|---|
| 1.) | AMV Reverse Transcriptase | AMV Reverse Transcriptase 5 x Reaction Buffer |
| 2.) | SuperScript III Reverse Transcriptase | 5 x First-Strand Buffer |

TABLE 35-continued

| Reverse Transcriptases and Buffers that are Used | |
|---|---|
| 3.) HIV Reverse Transcriptase | 10 x First-Strand Synthesis Buffer |
| 4.) M-MuLV Reverse Transcriptase | 10 x Reverse Transcriptase Reaction Buffer |
| 5.) Sensiscript Reverse Transcriptase | 10 x Buffer RT |

For the one-stage process of poly-A-reaction and reverse transcription (PAP+RT reaction), the reagents from Table 33 were pipetted together for reactions 1-5 (reaction buffer: buffer RT (Qiagen) as indicated in Table 36 and for reactions 6-9 (additional reverse transcriptases, in each case in the buffer that is supplied) as indicated in Table 37.

TABLE 33

| Materials for the Poly A Reaction and Reverse Transcription | |
|---|---|
| Poly (A) Polymerase | Ambion; Material Number 80 U: 2030 |
| AMV Reverse Transcriptase | Promega; Material Number 300 U: M5101 |
| SuperScript III Reverse Transcriptase | Invitrogen; Material Number 10,000 U: 18080-044 |
| HIV Reverse Transcriptase | Ambion; Material Number 500 U: #2045 |
| M-MuLV Reverse Transcriptase | BioLabs; Material Number 10,000 U: M0253S |
| Sensiscript RT Kit | Qiagen; Material Number 50 rxns: 205211 |
| Adenosine 5'-Triphosphate (rATP) | Amersham; Material Number 25 µmol: 27-2056-01 |
| RNase Inhibitor | Promega; Material Number: N2511 |
| Uni GAP dT Primer | 5'-TGG AAC GAG ACG ACG ACA GAC CAA GCT TCC CGT TCT CAG CCT TTT TTT TTT TTT TTT TTT TTV VN-3' (SEQ ID NO: 2) |
| Corn RNA | From 1 g of Ground Corn Husks with Qiagen RNeasy Mini Kit (Cat. No. 74106) Plant Protocol, 10-Fold Upscale (Maxi Shredder and Column) See Above |
| mleu7a Oligonucleotide | 5'-UGA GGU AGU AGG UUG UAU AGU U-3' (SEQ ID NO: 1) |

TABLE 36

PAP + RT Reaction in Buffer RT (Qiagen)

| Reagents | Final Concentration |
|---|---|
| 10x Buffer RT | 1x |
| rATP, 10 mmol | 1 mmol |
| Poly A Polymerase, 2 U/µl | 1 U |
| dNTP Mix (ATGC, 5 mmol each) | 0.5 mmol |
| Uni GAP dT Primer, 10 µmol | 1 µmol |
| RNase Inhibitor 10 U/µl | 10 U |
| 1.) AMV Reverse Transcriptase | 24 U |
| 2.) SuperScript III Reverse Transcriptase | 10 U |
| 3.) HIV Reverse Transcriptase | 1 U |
| 4.) M-MuLV Reverse Transcriptase | 10 U |

TABLE 36-continued

PAP + RT Reaction in Buffer RT (Qiagen)

| Reagents | Final Concentration |
|---|---|
| 5.) Sensiscript Reverse Transcriptase | 1 µl |
| RNase-Free Water | Variable |
| Mleu7a 10^9 Copies/µl | 2 µl (2 × 10^9 Copies) |
| Corn RNA, 20 ng/µl | 2 µl (40 ng) |
| Total Volume | 20 µl |
| Incubation | 1 Hour, 37° C. 5 Minutes, 93° C. |

TABLE 37

PAP + RT Reaction in Buffer Supplied with the Reverse Transcriptase

| Reagents | Final Concentration |
|---|---|
| 6.) AMV Reverse Transcriptase 5 x Reaction Buffer | 1x |
| 7.) 5 x First-Strand Buffer | 1x |
| 8.) 10 x First-Strand Synthesis Buffer | 1x |
| 9.) 10 x Reverse Transcriptase Reaction Buffer | 1x |
| rATP, 10 mmol | 1 mmol |
| Poly A Polymerase, 2 U/µl | 1 U |
| dNTP Mix (ATGC, 5 mmol each) | 0.5 mmol |
| Uni GAP dT Primer, 10 µmol | 1 µmol |
| RNase Inhibitor, 10 U/µl | 10 U |
| 6.) AMV Reverse Transcriptase | 24 U |
| 7.) 7.) SuperScript III Reverse Transcriptase | 10 U |
| 8.) HIV Reverse Transcriptase | 1 U |
| 9.) M-MuLV Reverse Transcriptase | 10 U |
| RNase-Free Water | Variable |
| mleu7a 10^9 Copies/µl | 2 µl (2 × 10^9 Copies) |
| Corn RNA, 20 ng/µl | 2 µl (40 ng) |
| Total Volume | 20 µl |
| Incubation | 1 Hour, 37° C. 5 Minutes, 93° C. |

Then, the samples were incubated for 1 hour at 37° C. Then, the reactions were heated for 5 minutes to 93° C., and thus the enzymes were inactivated.

Subsequently, in each case 2 µl was incorporated into an SYBR Green PCR for each reaction. The reactions were tested two times apiece. For this purpose, the reagents from Table 34 were pipetted together as indicated in Table 38, and the PCR was performed as indicated in Table 39.

TABLE 34

| Materials for the SYBR Green PCR (Table 34 discloses SEQ ID NOS 4 and 3, respectively, in order of appearance) | |
|---|---|
| QuantiTect SYBR Green PCR Kit (200) | Qiagen; Material Number: 204143 |
| let 7short (Specific miRNA Primer) | 5'-GAG GTA GTA GGT TGT ATA G-3' |
| Hum Uni Primer | 5'-AAC GAG ACG ACG ACA GAC-3' |

TABLE 38

| SYBR GREEN PCR | |
|---|---|
| Components for SYBR Green PCR | Final Concentration |
| 2x SYBR Green PCR Master Mix | 1x |
| Hum Uni Primer, 10 µmol | 0.5 µmol |
| let 7short (Specific miRNA Primer) | 0.5 µmol |
| RNase-Free Water | Variable |
| PAP + RT Reaction, Undiluted | 2 µl (2 × 10^8 Copies) |
| Final Reaction Volume | 20 µl |

TABLE 39

| 3-Step PCR Protocol | | |
|---|---|---|
| PCR Initial Reactivation | 15 Minutes, 95° C. | |
| Denaturation | 15 Seconds, 94° C. | 45x |
| Annealing | 30 Seconds, 52° C. | |
| Extension | 30 Seconds, 70° C. | |
| Melt Curve | | |

The PCR protocol consisted of an initial reactivation of the HotStarTaq polymerase contained in the QuantiTect SYBR Green PCR Master Mix for 15 minutes at 95° C., followed by 40 cycles for 15 seconds at 94° C., 30 seconds at 52° C., and 30 seconds at 72° C. (see Table 39). The acquisition of the fluorescence data was carried out during the 72° C. extension step. The PCR analyses were performed with an Applied Biosystems 7000 Real-Time PCR System (Applied Biosystems) in a reaction volume of 20 µl, and then a melt curve analysis was performed.

The amounts of reverse transcriptases used were optimized for standard reverse transcription reactions, which can be a likely explanation for the differences in the Ct value that are observed.

Example 7

Demonstration of the feasibility of a coupled, three-stage process of poly-A-reaction, reverse transcription and PCR in the same reaction vessel; effect of various additions to the efficiency of the detection of a 22-mer RNA oligonucleotide In this experiment, the feasibility of a coupled, three-stage process of the poly-(A)-polymerase reaction, reverse transcription and PCR in the same reaction vessel should be demonstrated. For this purpose, the coupled, three-stage process was performed with the indicated batches under the following conditions.

As a control, the reaction was performed in a two-stage process based on FIG. 1B.

For the three-stage process of poly-A-reaction, reverse transcription and PCR (PAP+RT reaction+PCR), the materials from Table 40 were put together as indicated in Table 41.

TABLE 40

| Materials for the Poly A Reaction, Reverse Transcription and PCR (Table 40 discloses SEQ ID NOS 2, 1, 4, 3, 9 and 20, respectively, in order of appearance) | |
|---|---|
| Poly (A) Polymerase | Epicenter Biotechnologies; Material Number 400 U: PAP5104 |
| QuantiTect Multiplex RT-PCR Kit | Qiagen; Material Number 200 rxns: 204643. |
| Adenosine 5'-Triphosphate (rATP) | Amersham; Material Number, 25 µmol: 27-2056-01 |
| dNTP Mix (ATGC, 10 mmol each) | Amersham; Material Number Qiagen Intern 1007430 |
| RNase Inhibitor | Promega; Material Number: N2511 |
| Uni GAP dT Primer | 5'-TGG AAC GAG ACG ACG ACA GAC CAA GCT TCC CGT TCT CAG CCT TTT TTT TTT TTT TTT TTT TTV VN-3' |
| Corn RNA | From 1 g of Ground Corn Husks with Qiagen RNeasy Mini Kit (Cat. No. 74106) Plant Protocol, 10-Fold Upscale (Maxi Shredder and Column) See Above |
| mleu7a Oligonucleotide | 5'-UGA GGU AGU AGG UUG UAU AGU U-3' |
| let 7short (Specific miRNA Primer) | 5'-GAG GTA GTA GGT TGT ATA G-3' |
| Hum Uni Primer | 5'-AAC GAG ACG ACG ACA GAC-3' |
| GAPDH-TM-HEX_BHQ<br>Poly A RNA<br>Random N8 Primer<br>Oligo dT 12 | 5'HEX-CAA GCT TCC CGT TCT CAG CC-BHQ 3' Amersham Biosciences Material Number 27-4110-01, Dissolved with 25 µg/µl in RNase-Free Water NNNNNNNN TTTTTTTTTTTT-3' Phosphate |

TABLE 41

| PAP + RT Reaction + PCR with Batches in QuantiTect Multiplex RT-PCR Master Mix (Qiagen) | |
|---|---|
| Reagents | Final Concentration |
| 2x QuantiTect Multiplex RT-PCR Master Mix | 1 x |
| rATP, 10 mmol | 100 µmol |
| Poly A Polymerase, 4 U/µl | 1 U |
| dNTP Mix (ATGC, 10 mmol each) | 0.5 mmol |
| Uni GAP dT Primer, 10 µmol | 0.05 µmol |
| RNase Inhibitor, 40 U/µl | 10 U |
| QuantiTect Multiplex RT Mix | 0.2 µl |
| Hum Uni Primer, 10 µmol | 0.5 µmol |
| let 7short (Specific miRNA Primer) | 0.5 µmol |
| GAPDH-TM-HEX_BHQ | 0.2 µmol |
| RNase-Free Water | Variable |
| Poly A RNA, 25 µg/µl | 10 ng/µl |
| N8 Random Primer | 0.05 µmol |
| Oligo dT12 | 5 µmol |
| mleu7a 10^9 Copies/µl | 2 µl (2 × $10^9$ Copies) |
| Corn RNA, 20 ng/µl | 2 µl (40 ng) |
| Total Volume | 20 µl |

The reactions were tested three times apiece. For this purpose, the reagents from Table 40 were pipetted together as indicated in Table 41, and the reaction was performed as indicated in Table 42.

TABLE 42

| Reaction Protocol of the "3-in-1" Reaction | | |
|---|---|---|
| Poly A Reaction and | 45 Minutes, 37° C. | |
| Reverse Transcription | 15 Minutes, 50° C. | |
| PCR Initial Reactivation | 15 Minutes, 95° C. | |
| Denaturation | 15 Seconds, 94° C. | 45x |
| Annealing/Extension | 30 Seconds, 52° C. | |

The reaction protocol first consisted of conditions for the combined reaction of poly-A polymerase and reverse transcription with the QuantiTect Multiplex Reverse Transcriptase Mix (45 minutes, 37° C., and 15 minutes, 50° C.). From this followed an incubation for 15 minutes at 95° C., with the purpose of inactivating the poly-A-polymerase and reverse transcriptase and activating the HotStarTaq DNA polymerase that is contained in the QuantiTect Multiplex RT-PCR Master Mix. 45 PCR cycles followed for 15 seconds at 94° C. and for 30 seconds at 52° C. (see Table 43) to amplify the generated let7a-cDNA in a real-time PCR. For detection, a fluorescence-labeled probe specific to the 5'-tail of the Uni Gap dT primer was used. The acquisition of the fluorescence data was carried out during the 52° C. annealing/extension step. The "3-in-1" reaction was performed with an Applied Biosystems 7500 Fast Real-Time PCR System (Applied Biosystems) in a reaction volume of 20 μl.

As shown in FIG. 14, the "3-in-1" reaction allows the specific detection of the synthetic 22mer RNA oligonucleotide in the background of corn RNA. The sample, which contains the synthetic 22mer RNA oligonucleotide in the background of corn RNA, supplies a Ct value of 20.61, whereby the control reaction with corn RNA yielded a Ct value of 309.65. This experiment shows that the "3-in-1" reaction can technically be used under the given conditions.

Example 8

Implementation of the "3-in-1" process according to the invention with use of a manual PCR primer "Hot Starts," with the purpose of promoting the reaction of the coupled, three-stage process. As a control, the reaction was performed in a two-stage process based on FIG. 1B.

The reactions were put together with the materials indicated in Table 43 as indicated in Table 44.

TABLE 43

| Materials for the Poly A Reaction, Reverse Transcription and PCR (Table 43 discloses SEQ ID NOS 2, 1, 4, 3 and 20, respectively, in order of appearance) | |
|---|---|
| Poly (A) Polymerase | Epicenter Biotechnologies; Material Number 400 U: PAP5104 |
| QuantiTect Multiplex RT-PCR Kit | Qiagen; Material Number 200 rxns: 204643 |
| Adenosine 5'-Triphosphate (rATP) | Amersham; Material Number 25 μmol: 27-2056-01 |
| dNTP Mix (ATGC, 10 mmol each) | Amersham; Material Number Qiagen Intern 1007430 |
| RNase Inhibitor | Promega; Material Number: N2511 |
| Uni GAP dT Primer | 5'-TGG AAC GAG ACG ACG ACA GAC CAA GCT TCC CGT TCT CAG CCT TTT TTT TTT TTT TTT TTT TTV VN-3' |
| Corn RNA | From 1 g of Ground Corn Husks with Qiagen RNeasy Mini Kit (Cat. No. 74106) Plant Protocol, 10-Fold Upscale (Maxi Shredder and Column) See Above |
| mleu7a Oligonucleotide | 5'-UGA GGU AGU AGG UUG UAU AGU U-3' |
| PCR Primer: | |
| let 7short (Specific miRNA Primer) | 5'-GAG GTA GTA GGT TGT ATA G-3' |
| Hum Uni Primer | 5'-AAC GAG ACG ACG ACA GAC-3' |
| GAPDH-TM-HEX_BHQ Additions: Poly A RNA Random N8 Primer Oligo dT 12 | Amersham Biosciences Material Number 27-4110-01, Dissolved with 25 μg/μl in RNase-Free Water NNNNNNNN TTTTTTTTTTTT-3' Phosphate |

TABLE 44

| PAP + RT Reaction + PCR in QuantiTect Multiplex RT-PCR Master Mix (Qiagen) | |
|---|---|
| Reagents | Final Concentration |
| 2x QuantiTect Multiplex RT-PCR Master Mix | 1 x |
| rATP, 10 mmol | 100 μmol |
| Poly A Polymerase, 4 U/μl | 1 U |
| dNTP Mix (ATGC, 5 mmol each) | 0.5 mmol |
| Uni GAP dT Primer, 10 μmol | 0.05 μmol |
| RNase Inhibitor, 40 U/μl | 10 U |
| QuantiTect Multiplex RT Mix | 0.2 μl |
| RNase-Free Water | Variable |
| Poly A, 25 μg/μl | 10 ng/μl |
| N8 Random Primer | 0.05 μmol |
| Oligo dT12 | 5 μmol |
| mleu7a 10^9 Copies/μl | 2 μl (2 × $10^9$ Copies) |
| Corn RNA, 20 ng/μl | 2 μl (40 ng) |
| Total Volume | 20 μl |

With the PCR primers from Table 45, a primer mix is produced, and the required amount for respectively one reaction is pipetted in each case into a cover of an optical cap (covers for real-time PCR vessels, Applied Biosystems; Material Number 4323032). Then, the cover was incubated on a heating block at 37° C. for about 20 minutes until the liquid was evaporated, and thus the primer was dried.

After the complete drying of the PCR primer in the cover, the reagents are pipetted together as in Table 44 and added in Optical Tubes (real-time PCR vessels, Applied Biosystems; Material Number 4316567), sealed with the pretreated optical caps, and the PCR is performed as indicated in Table 47.

The reactions were tested three times apiece.

TABLE 45

| Composition of Dried Oligo-Mix in the PCR Cover | | |
|---|---|---|
| | Amount of Oligo/rxn | Final Concentration in PCR After the Redissolution |
| Hum Uni Primer | 10 pmol | 0.5 μmol |
| let 7short (Specific miRNA Primer | 10 pmol | 0.5 μmol |
| GAPDH-TM-HEX_BHQ | 4 pmol | 0.2 μmol |

TABLE 46

| Reaction Protocol of the "3-in-1" Reaction | | |
|---|---|---|
| Poly A Reaction and | 45 Minutes, 37° C. | — |
| Reverse Transcription | 15 Minutes, 50° C. | |
| Incubation | 95° C., 3 Minutes | |
| Briefly Invert 8-Strip Reaction Vessel to Dissolve the Primer, Dried in the Cover, in the Reaction Mix | | |
| PCR Initial Reactivation | 12 Minutes, 95° C. | |
| Denaturation | 15 Seconds, 94° C. | 45x |
| Annealing/Extension | 30 Seconds, 52° C. | |

The reaction protocol first consisted of conditions for the combined reaction of poly-A polymerase and the reverse transcription with the QuantiTect Multiplex Reverse Transcriptase Mix (45 minutes, 37° C., and 15 minutes, 50° C.). Then, the reactions were heated for 3 minutes to 95° C. with the purpose of inactivating the poly-A-polymerase and reverse transcriptase enzymes. Then, the PCR tubes were briefly removed from the device and inverted, with the purpose of redissolving the dried primer that is present in the covers and making it available for the following PCR reaction. An incubation followed from this for 12 minutes at 95° C. to activate the HotStarTaq DNA polymerase contained in the QuantiTect Multiplex RT-PCR Master Mix. A reactivation that is shorter by 3 minutes was selected here, since the reaction mix was already heated previously for inactivating the poly-A-polymerase and reverse transcriptase enzymes for 3 minutes to 95° C. 45 PCR cycles followed for 15 seconds at 94° C. and 30 seconds at 52° C. (see Table 47) to amplify the generated let7a-cDNA in a real-time PCR. For detection, a fluorescence-labeled probe specific to the 5'-tail of the Uni Gap dT Primer was used. The acquisition of the fluorescence data was carried out during the 52° C. annealing/extension step. The "3-in-1" reaction was performed with an Applied Biosystems 7500 Real-Time PCR System (Applied Biosystems) in a reaction volume of 20 μl.

Figures

FIG. 1 shows a comparison between the one-stage process according to this invention (B) and the two-stage process as it is known in the prior art (A). Poly A polymerase: enzyme with polyadenylenation activity in terms of the invention, reverse transcriptase: enzyme with reverse transcription activity in terms of the invention; rATP: ribonucleotide, here adenosine-5'-triphosphate by way of example; dNTP: deoxyribonucleotides; oligo dT tail primer: anchor oligonucleotide with various possible embodiments in terms of the invention; Uni GAP dT primer: special embodiment of the anchor oligonucleotide; tail: 5' tail as an optional part of the anchor oligonucleotide; w: defines the length according to the invention of the homopolymer tail that is attached by the polyadenylation activity (greater than 10-20 bases); x, y: defines the type and length according to the invention of the 3'-anchor sequence of the anchor oligonucleotide according to the invention; z: defines the length of the homopolymer portion of the anchor oligonucleotide according to the invention. FIG. 1 discloses "AAAAA$[A]_{1-w}$" as SEQ ID NO: 21.

FIG. 2 shows a graphic depiction of the Ct values from Table 6: Condition a) contained templates in each case, and in condition b), only $H_2O$, instead of templates, was added ($H_2O$ in PAP reaction). In b), no signal up to PCR cycle 40 (maximum number of the cycles performed) was obtained, therefore the indication is "No Ct."

FIG. 3 shows an agarose gel analysis of the real-time PCR products from Example 1. M: 100 bp ladder (Invitrogen, Catalog No. 15628-050). 2% Agarose, colored with ethidium bromide in TAE as a running buffer. Loading diagram: Trace 1: markers, then in each case the 3× determinations have been plotted next to one another: 1a, 1b, 2a, 2b, 3a, 3b, 4a, 4b.

In 2, 4 and 5 with standard RT, a signal was detected at the earliest only after cycle 38 or in 2), no signal, therefore the indication is "no Ct."

Figure 1A:
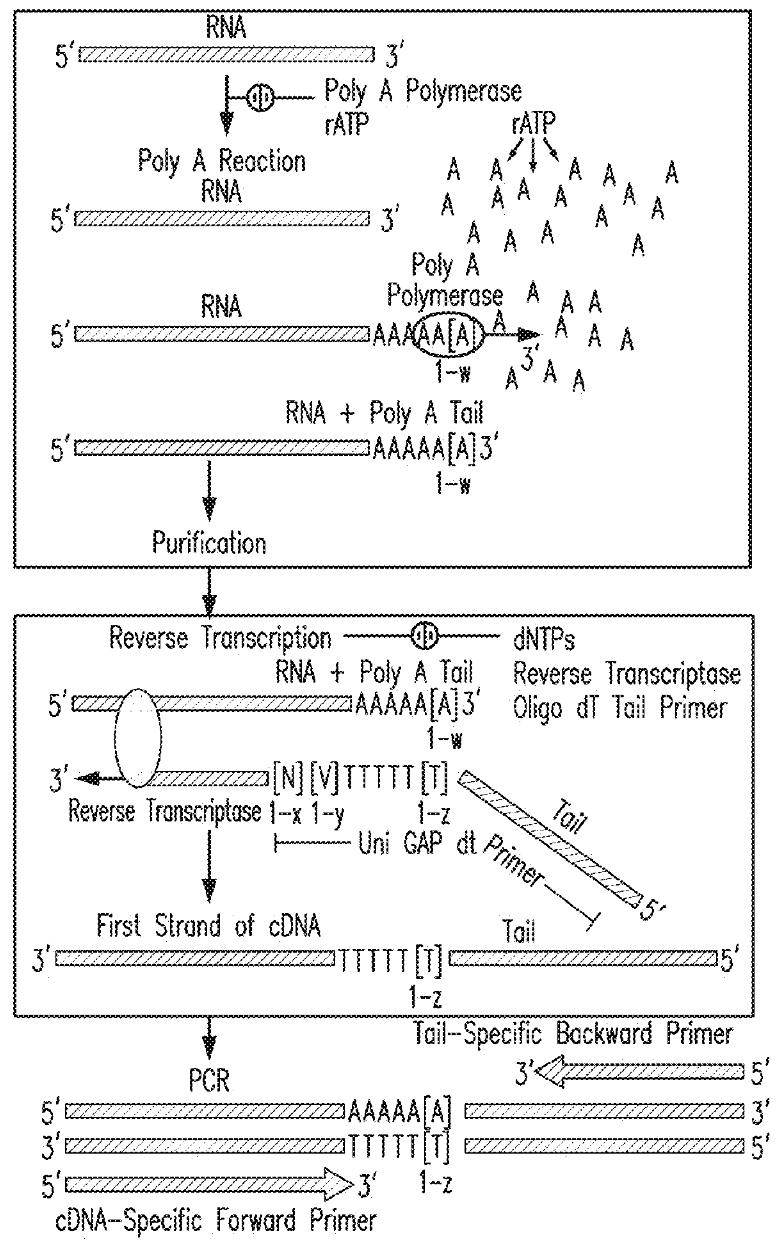
Figure 1B:
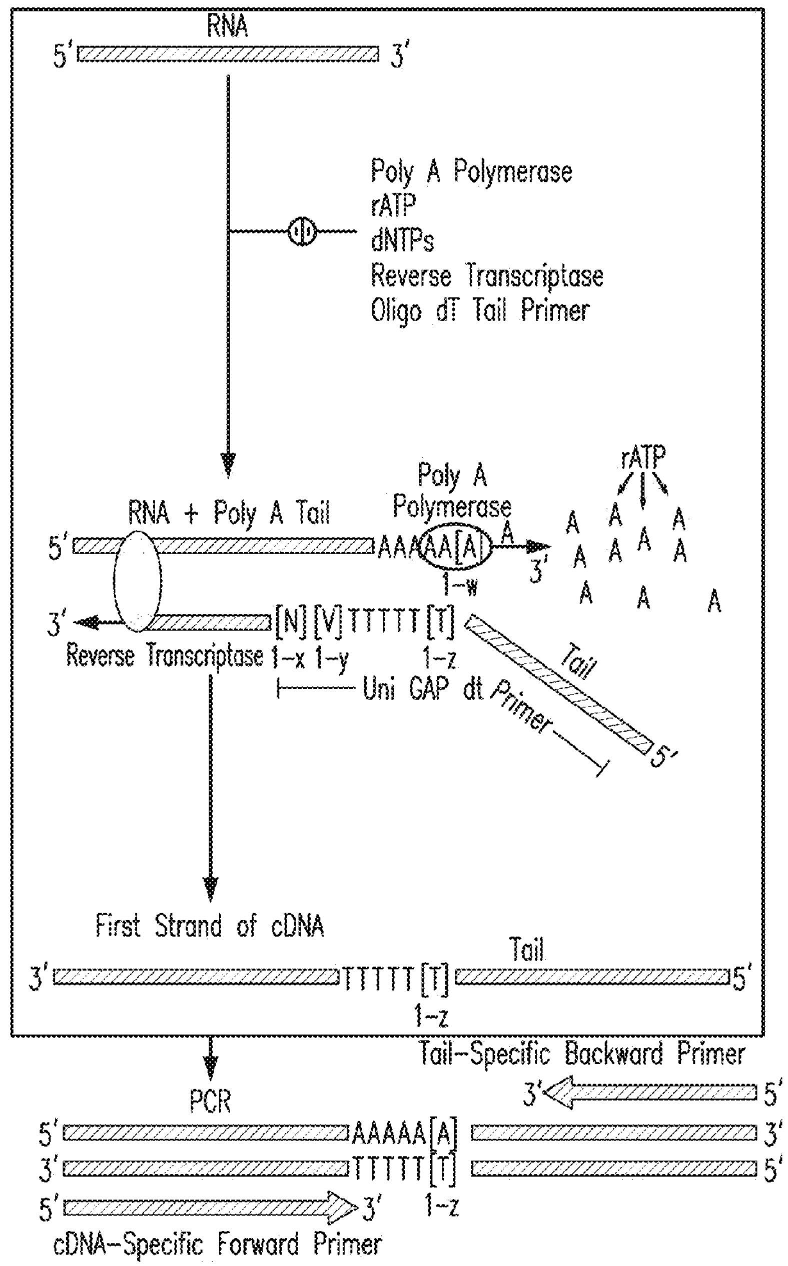
Figure 2:
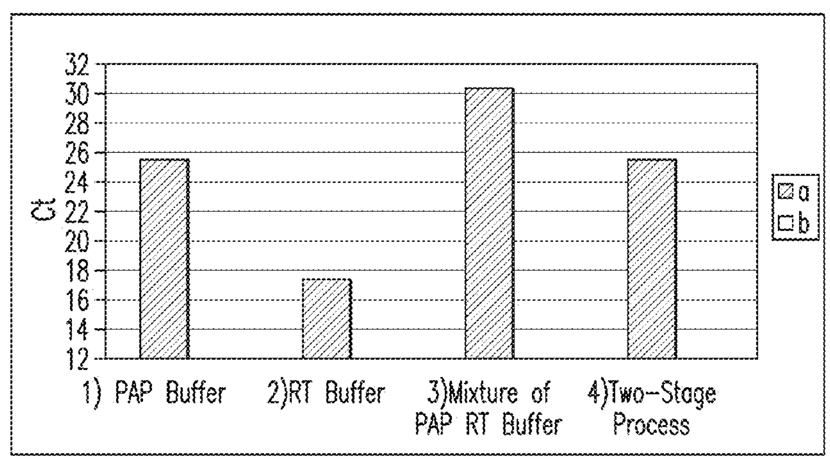
Figure 3:
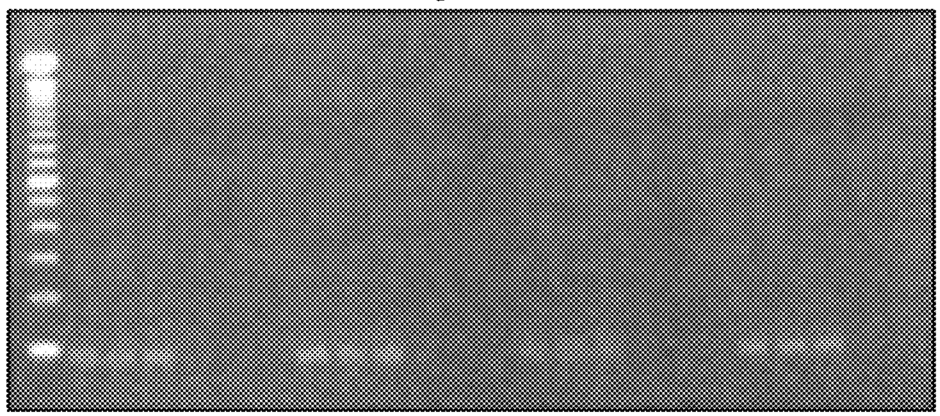
Figures 4, 5:
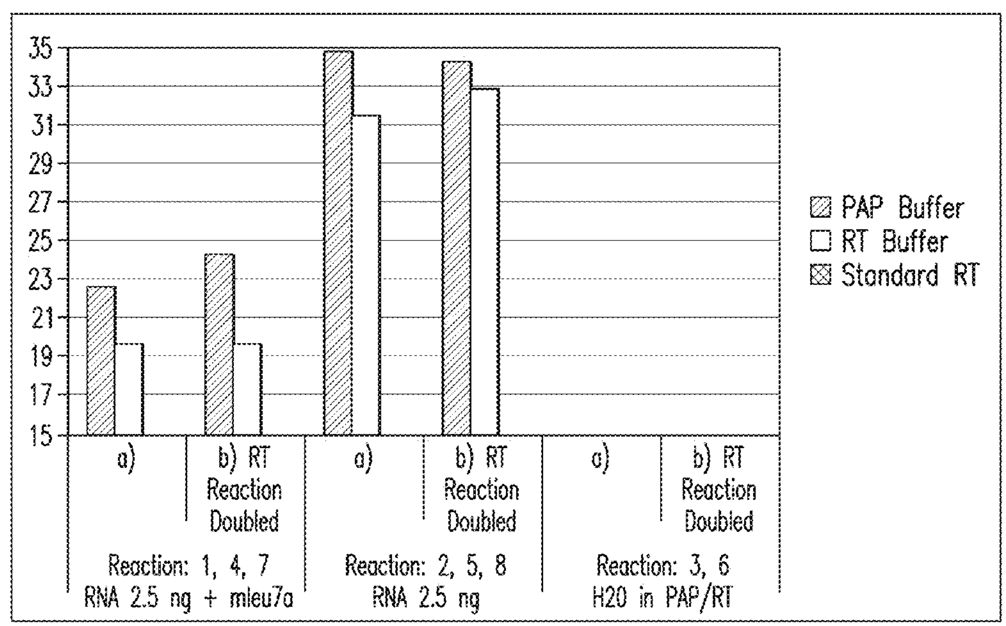
FIG. 4 shows a tabular depiction of Ct values that were obtained by real-time PCR analysis of the reaction products of the batches described in Table 8. At 3 and 6, no signal up to PCR cycle 40 (maximum number of the cycles performed) was obtained; therefore the indication is "no Ct."
FIG. 5 shows a graphic depiction of Ct values that were obtained by real-time PCR analysis of the reaction products of the batches described in Table 8.
Figures 6, 7:
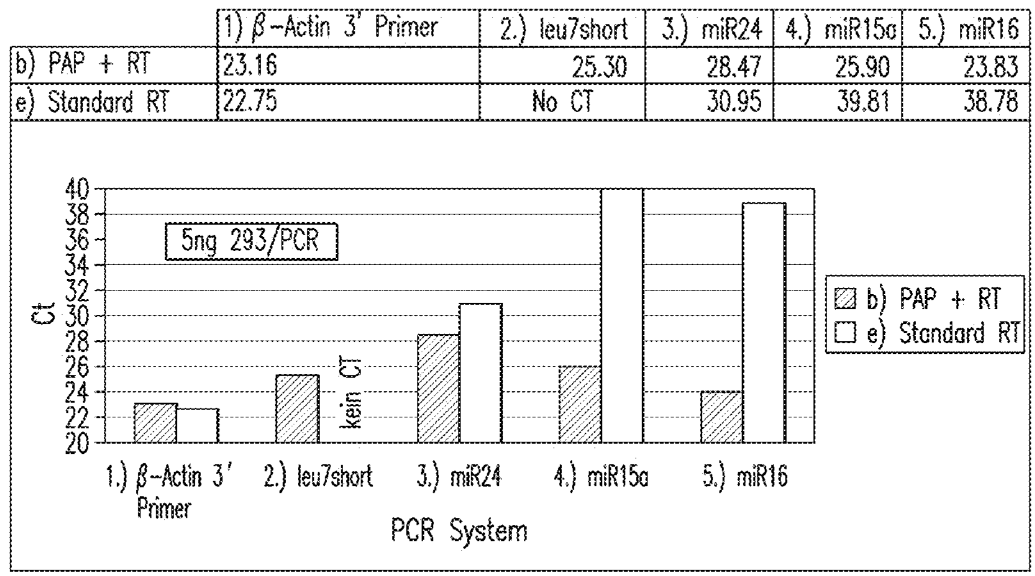
FIG. 6 shows a tabular depiction of Ct mean values that were obtained by real-time PCR analysis of the reaction products of the batches b) and e) described in Table 18.

FIG. 7 shows a tabular depiction of real-time PCR results of batches b) and d) from Table 18, as well as the controls with only one primer from Table 19, batches a)-d). No signal up to PCR cycle 40 (maximum number of the cycles performed) was obtained; therefore the indication is "no Ct."

Figure 8:
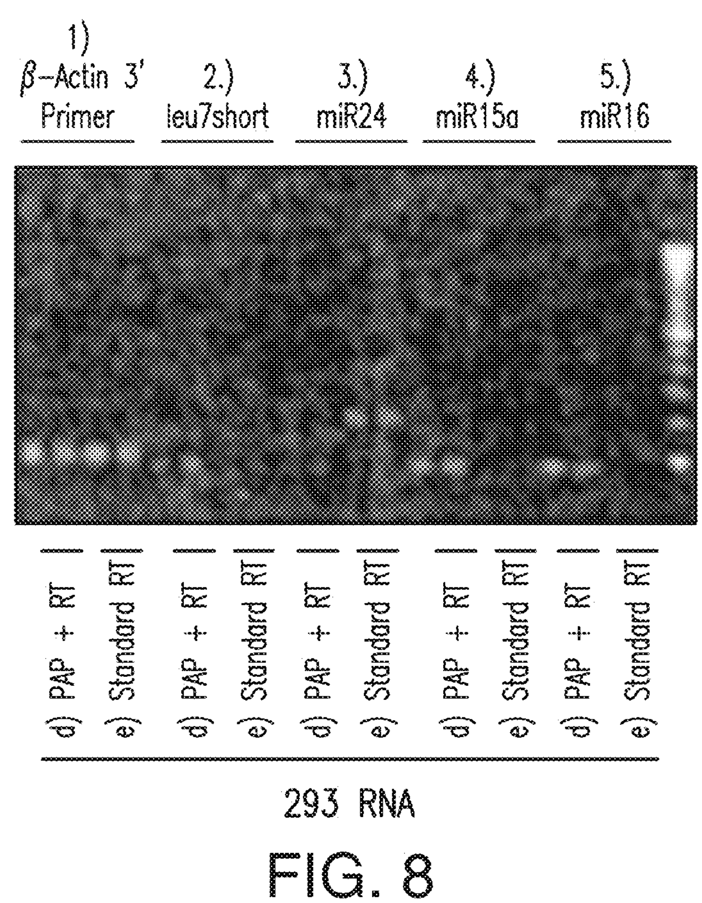

FIG. 8 shows an agarose gel analysis of the real-time PCR products from Example 3. M: 100 bp ladder (Invitrogen, catalog No. 15628-050). 2% Agarose, colored with ethidium bromide in TAE as a running buffer.

Figure 9:
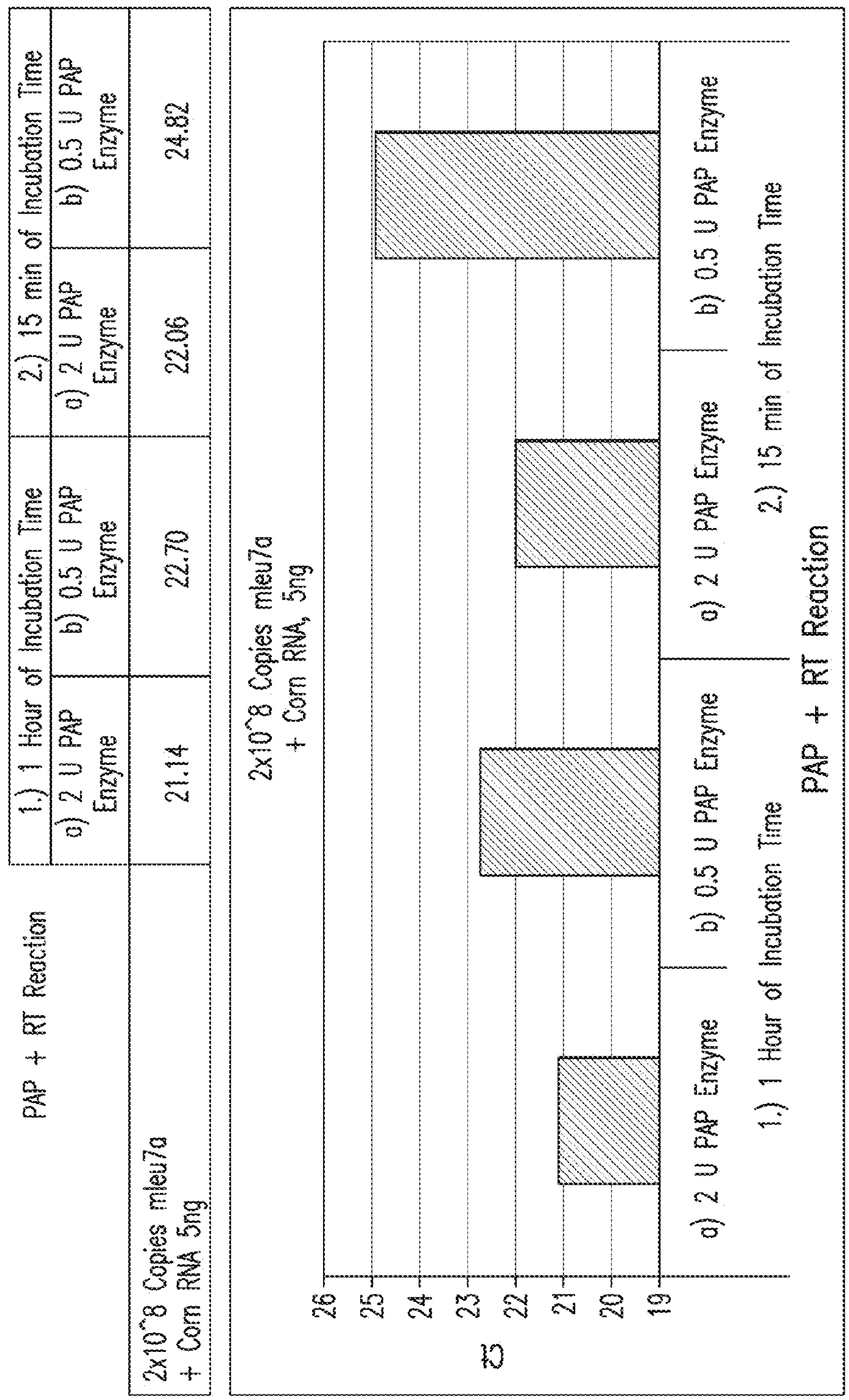

FIG. 9 shows a tabular depiction of Ct mean values that were obtained by real-time PCR analysis of the reaction products of the batches 1a), b) and 2a), b) described in Table 30.

Lower Part: Graphic depiction of Ct mean values that were obtained by real-time PCR analysis of the reaction products of the batches described in Table 30.

Figure 10:
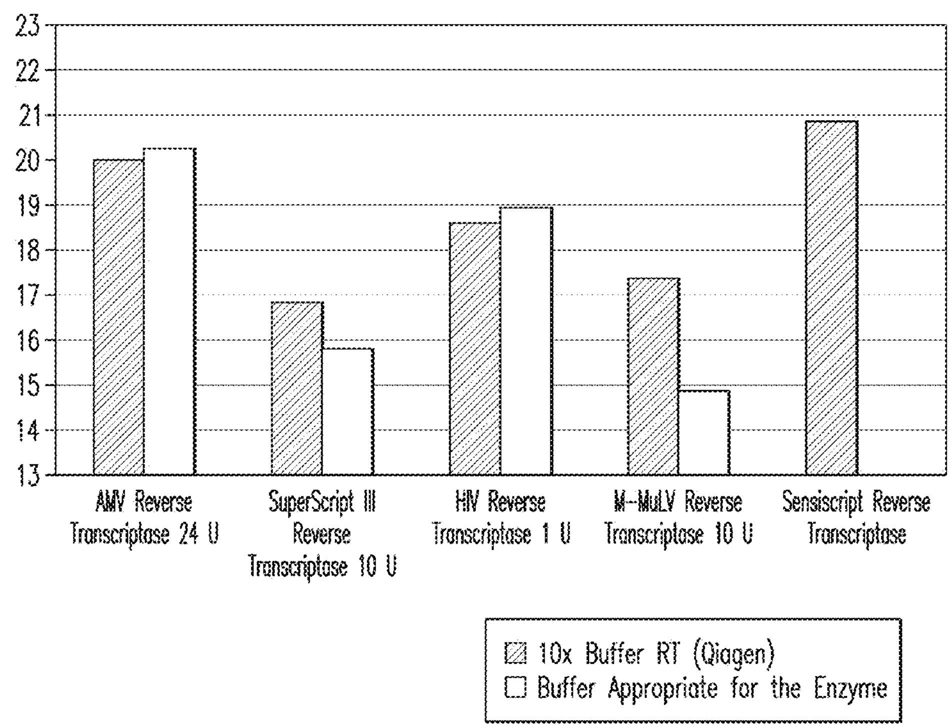

FIG. 10 shows a tabular depiction of the Ct mean values that were obtained by real-time PCR analysis of the reaction products of the batches described in Table 36, 1-5, and in Table 37, 6-9.

Lower Part: Graphic depiction of Ct mean values that were obtained by real-time PCR analysis of the reaction products of the batches described in Table 36, 1-5 and in Table 37, 6-9.

FIG. 11 shows a list of the nucleic acid sequences used.

FIG. 12 shows anchor oligonucleotides according to the invention. FIG. 12 discloses "poly (T) 15-50" as SEQ ID NO: 22 and "Anchor Oligonucleotides" as SEQ ID NOS 23-26, 26-27 and 10-19, respectively, in order of appearance.

Figure 13A:
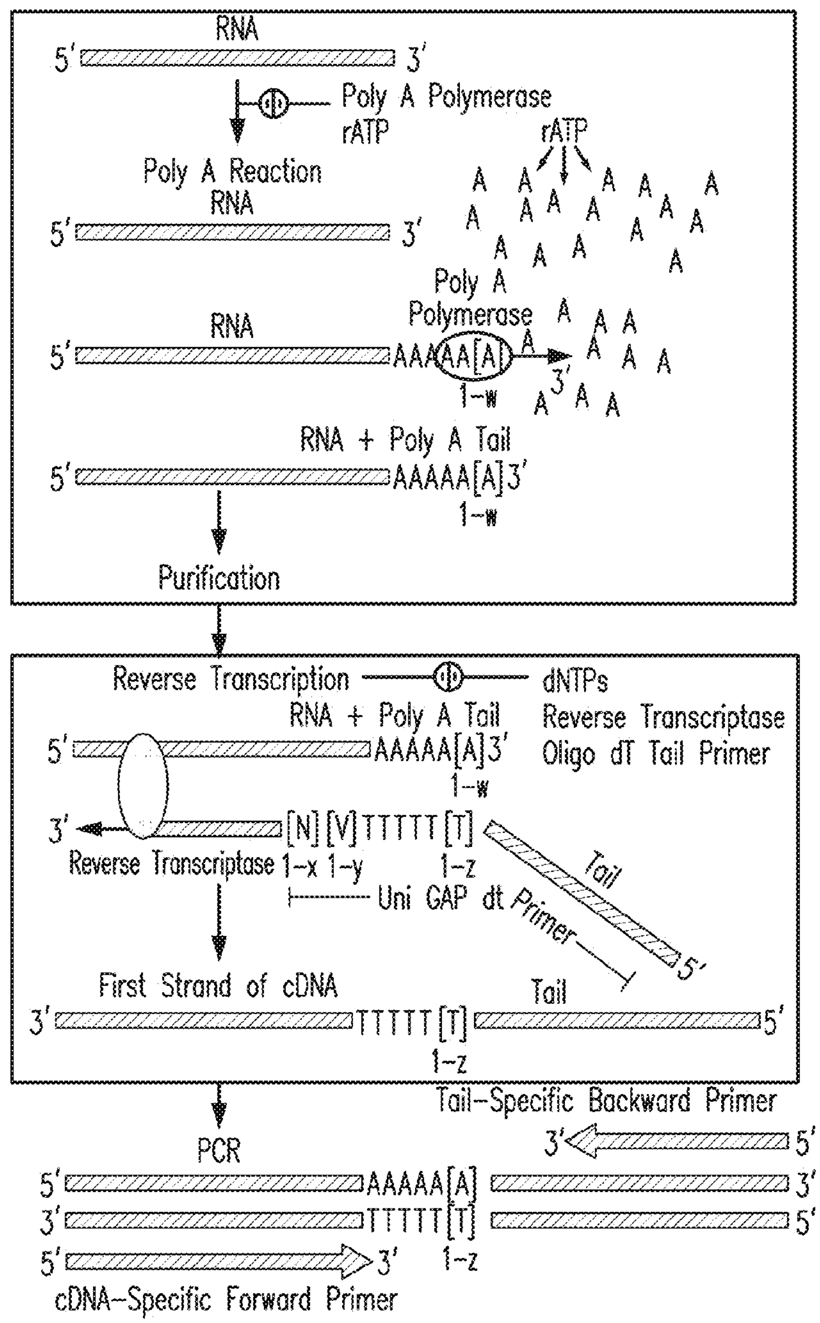
Figure 13B:
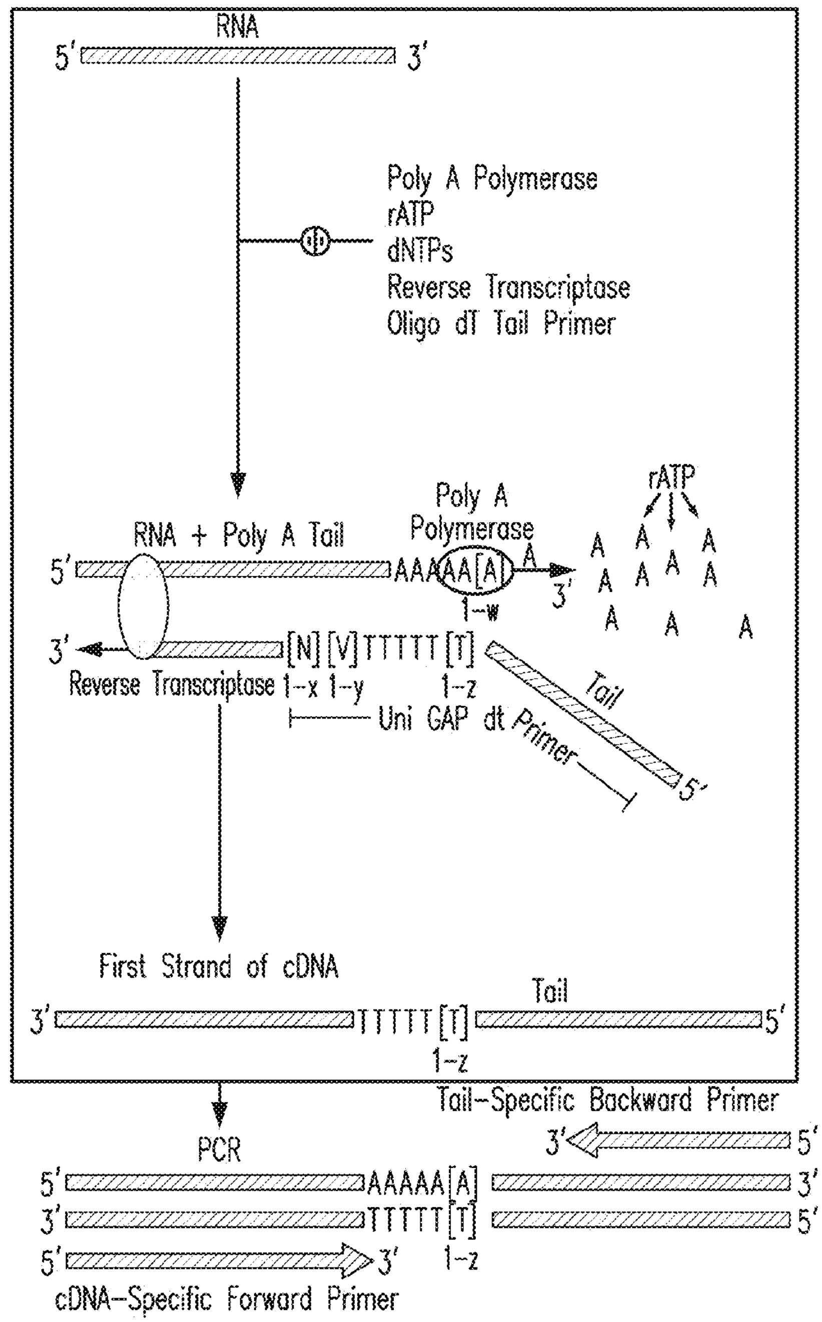

FIG. 13 shows a comparison between the one-stage "3-in-1" process according to this invention (B) and the three-stage process as it is known in the prior art (A). PolyA polymerase: enzyme with polyadenylation activity in terms of the invention; FIG. 13 discloses "AAAAA$[A]_{1-w}$" as SEQ ID NO: 21.

Reverse transcriptase: enzyme with reverse transcriptase activity in terms of the invention;

rATP: ribonucleotide, here adenosine-5'-triphosphate by way of example; dNTPs: deoxyribonucleotides;

Oligo dT tail primer: anchor oligonucleotide with various possible embodiments in terms of the invention;

Uni GAP dT primer: special embodiment of the anchor oligonucleotide;

Tail: 5'-Tail as an optional part of the anchor oligonucleotide;

w: defines the length, according to the invention, of the homopolyer tails that are attached by the polyadenylation activity (greater than 10-20 bases);

x, y: defines the type and length, according to the invention, of the 3'-anchor sequence of the anchor oligonucleotide according to the invention;

z: defines the length of the homopolymer portion of the anchor oligonucleotide according to the invention.

PCR primer: at least one oligonucleotide for specific detection of the cDNA species, optionally at least one probe;

PCR enzyme: enzymatic activity that allows the specific detection of the cDNA species contained in the sample.

Figure 14:
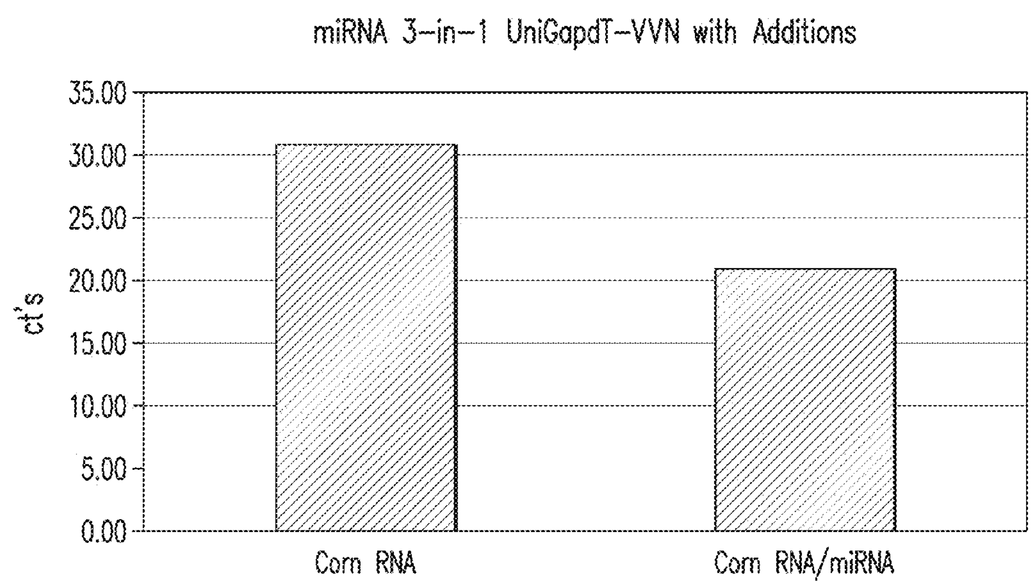

FIG. 14 shows a tabular depiction of the Ct mean values of a "3-in-1" reaction, i.e., the combined poly-(A)-polymerase reaction, reverse transcription and real-time PCR analysis coupled in a reaction vessel, according to the reaction batch from Example 7 corresponding to Table 41 and the reaction batch from Table 42.

Lower Part: Graphic depiction of Ct mean values of a "3-in-1" reaction, i.e., the combined poly-(A)-polymerase reaction, reverse transcription and real-time PCR analysis coupled in a reaction vessel, according to the reaction batch from Example 7 corresponding to Table 41 and the reaction batch from Table 42.

Figure 15:
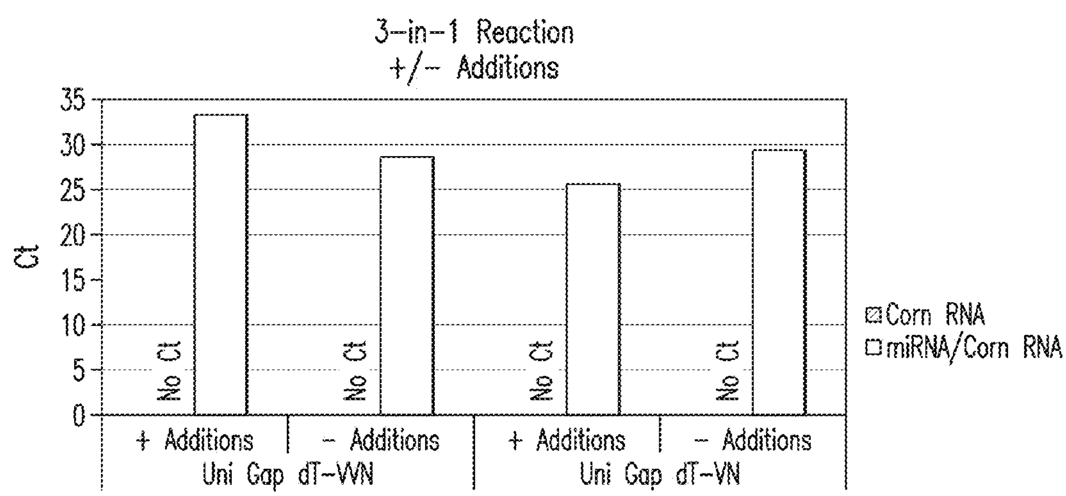

FIG. 15 shows a tabular depiction of Ct mean values of a "3-in-1" reaction, i.e., the combined poly-(A)-polymerase reaction, reverse transcription and real-time PCR analysis coupled in a reaction vessel, after the reaction batch of Example 8 corresponding to Table 44 and the reaction batch from Table 46.

Lower Part: Graphic depiction of Ct mean values of a "3-in-1" reaction, i.e., the combined poly-(A)-polymerase reaction, reverse transcription, and real-time PCR analysis coupled in a reaction vessel.

Figure 16:
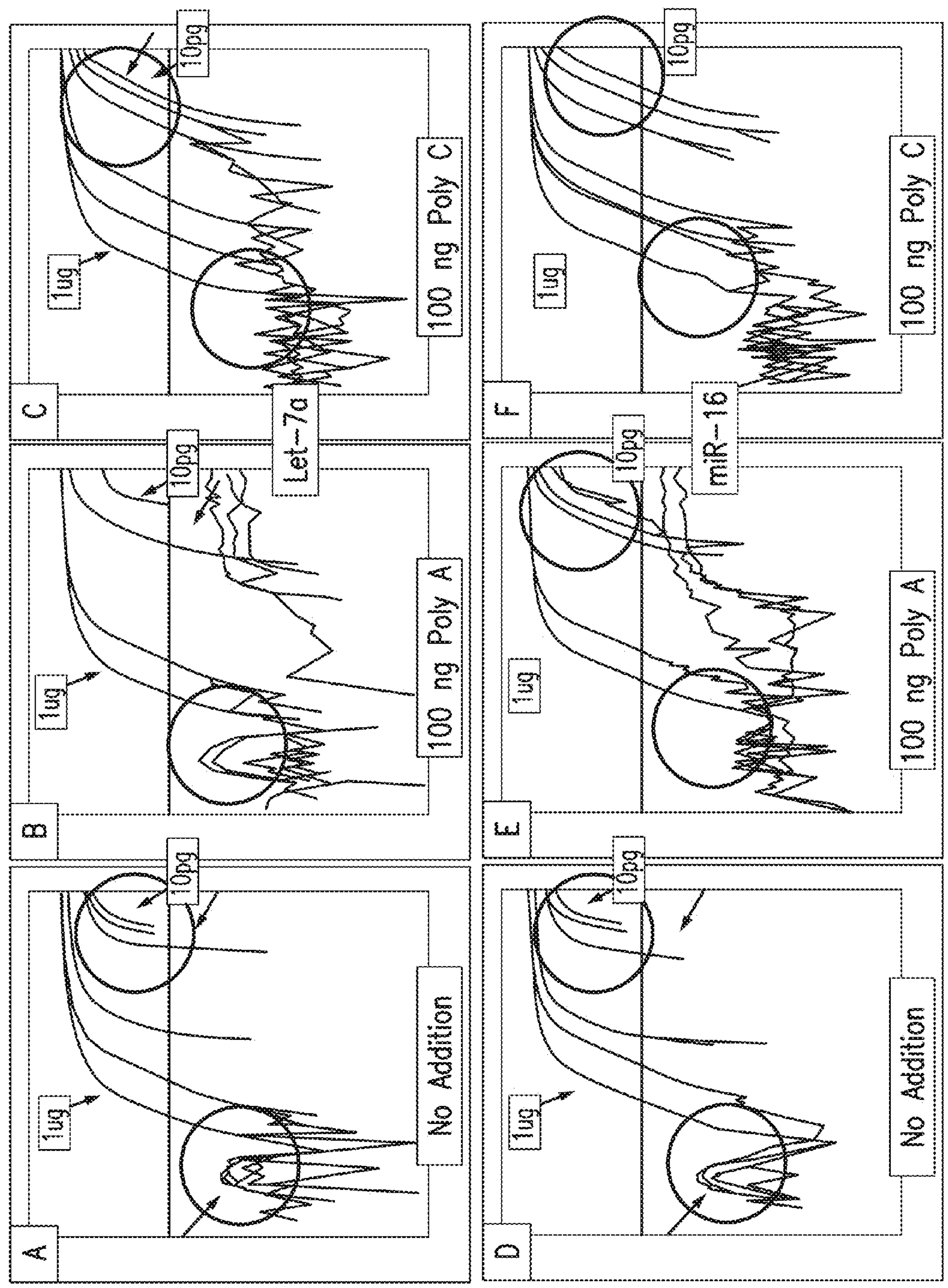

FIG. 16 shows various amounts (10 pg to 1 μg) of miRNAeasy RNA, which were reverse transcribed with use of miScript in the presence or absence of 100 ng of poly-(A) or poly-(C). The thus produced cDNA was used in a real-time PCR; in this case, miR-16 and let-7a were tested.

Figure 17:
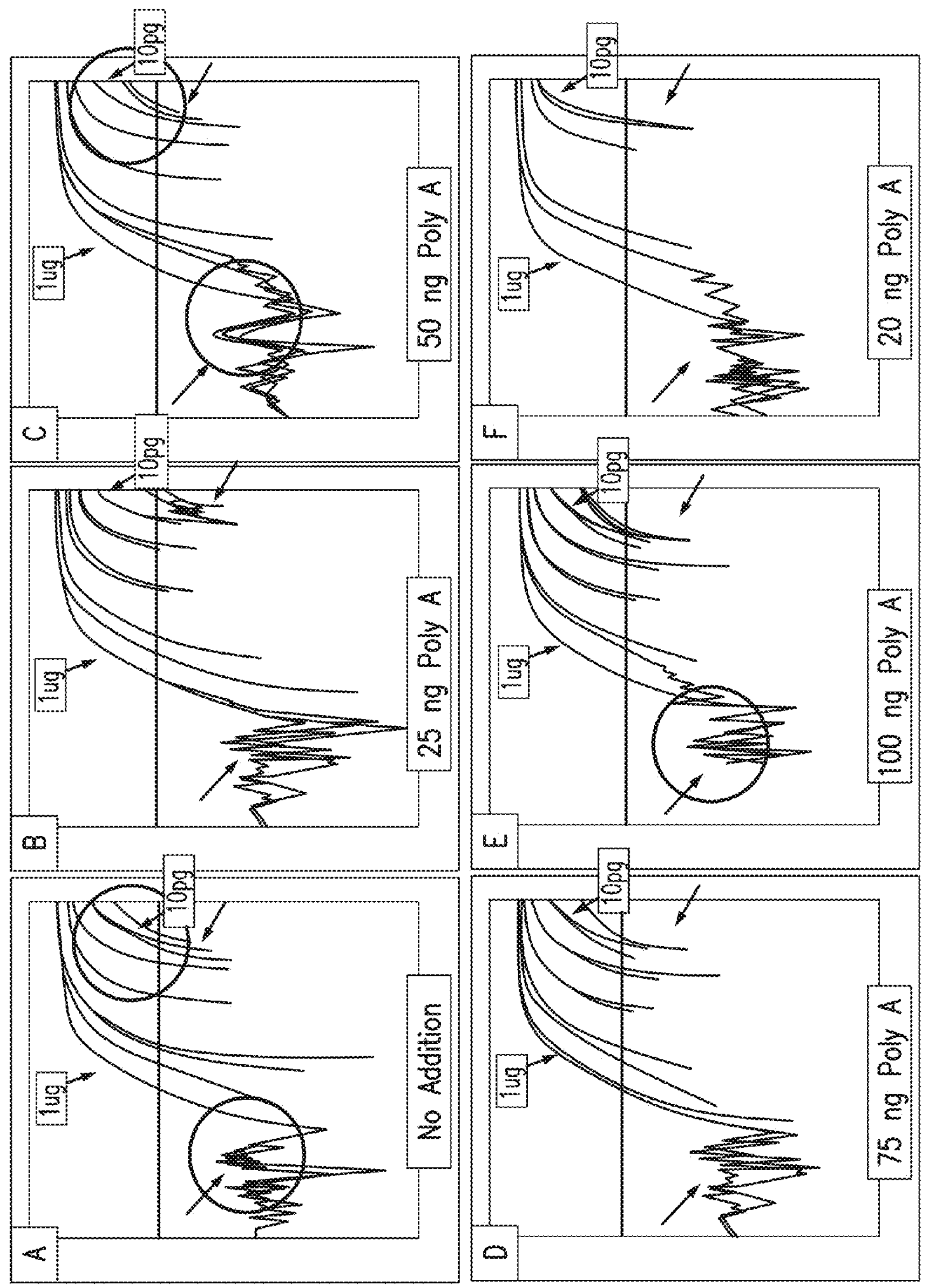

FIG. 17 shows various amounts (10 pg to 1 μg) of miRNAeasy RNA, which were reverse transcribed with use of miScript in the presence or absence of various amounts of poly(A). The thus produced cDNA was used in a real-time PCR; in this case, miR-16 was tested.

Figure 18:
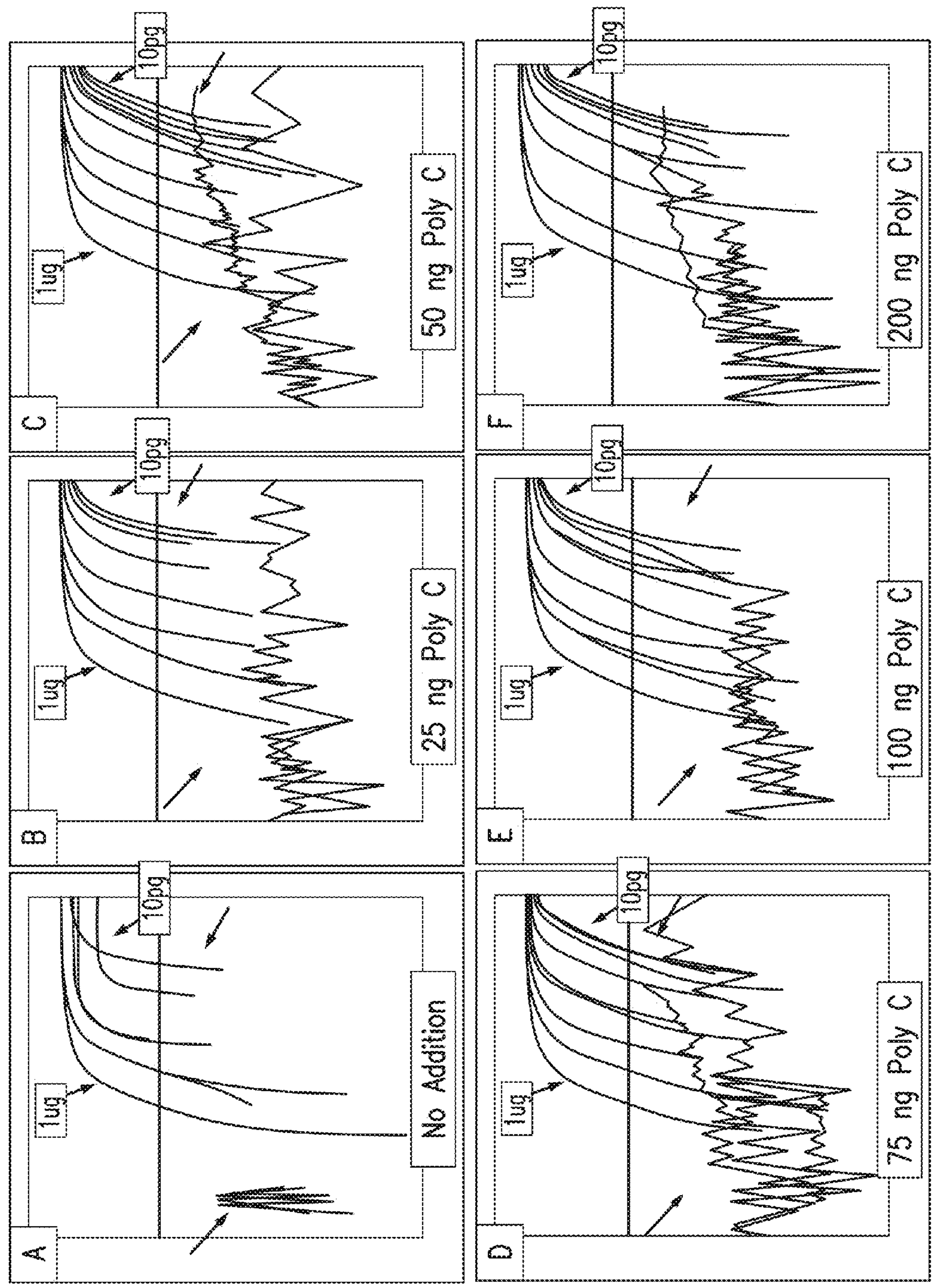

FIG. 18 shows various amounts (10 pg to 1 μg) of miRNAeasy RNA, which were reverse transcribed with use of miScript in the presence or absence of various amounts of poly-(C). The thus produced cDNA was used in a real-time PCR; in this case, miR-16 was tested.

Figure 19:
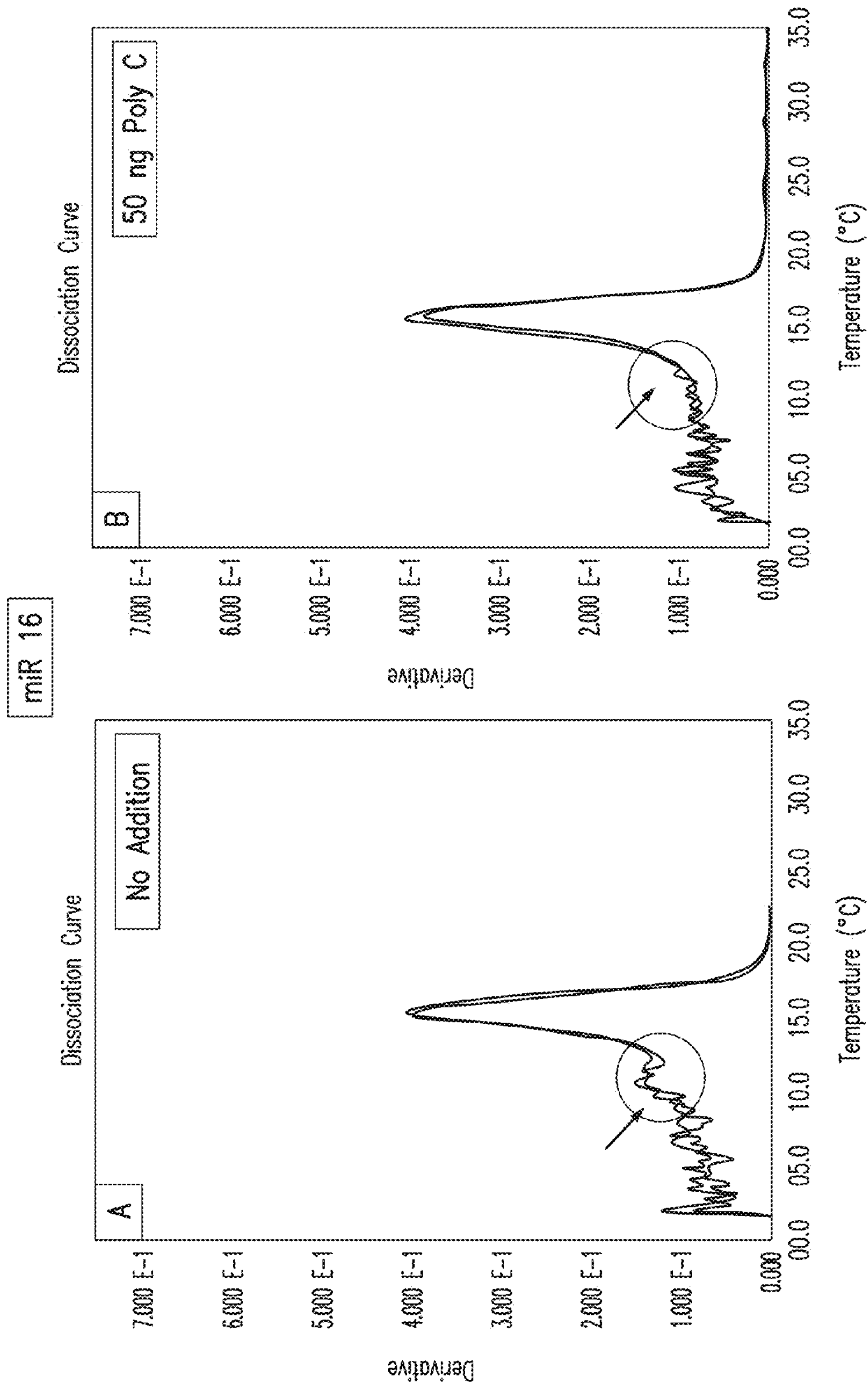

FIG. 19 shows the use of 10 pg of miRNeasy RNA, which was reverse transcribed in the presence or absence of 50 ng of poly-(C) with use of the miScript RT Kit. The thus produced cDNA was used in a real-time PCR to detect GAPDH.

Figure 20:
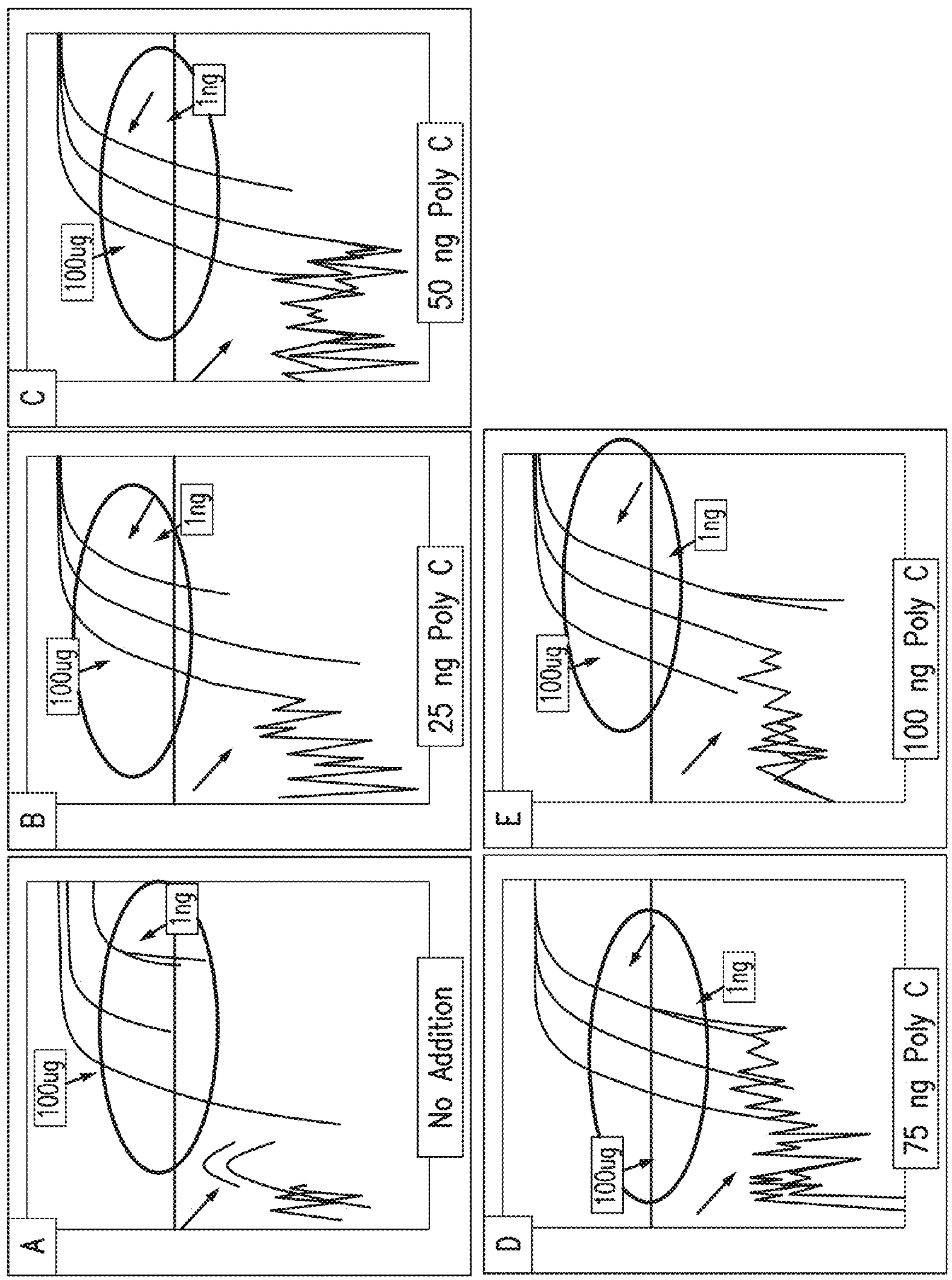

FIG. 20 shows various amounts (1-100 ng) of miRNeasy RNA, which were reverse transcribed with use of miScript in the presence or absence of various amounts of poly-(C). The thus produced cDNA was used in a real-time PCR, in this case to test GADPH.

Figure 21:
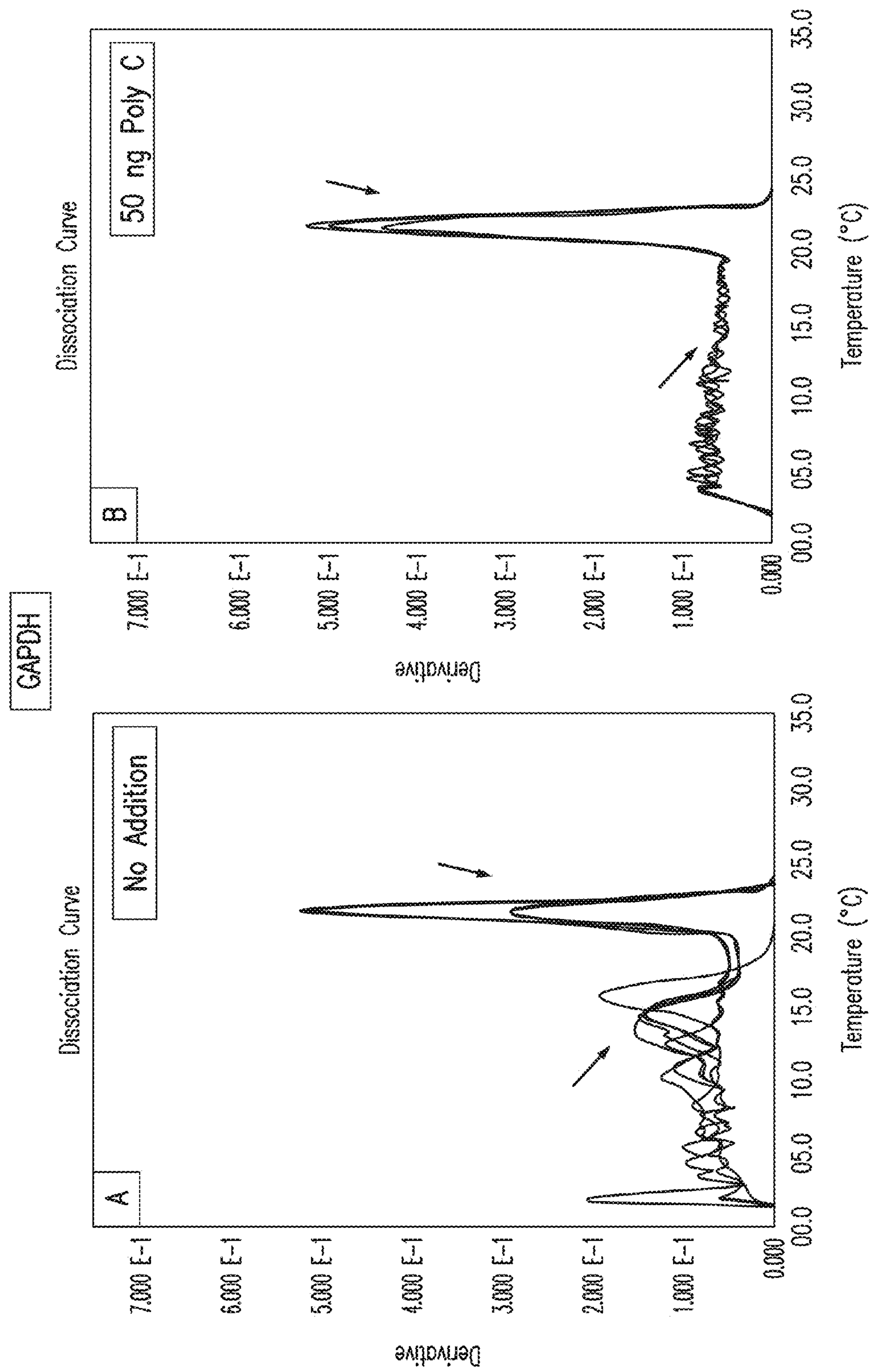

FIG. 21 shows the use of 10 and 100 pg of miRNeasy RNA, which were reverse transcribed in the presence or absence of 50 ng of poly-(C) and with use of the miScript RT Kit. The thus produced cDNA was tested in a real-time PCR to detect GAPDH.

Figure 22:
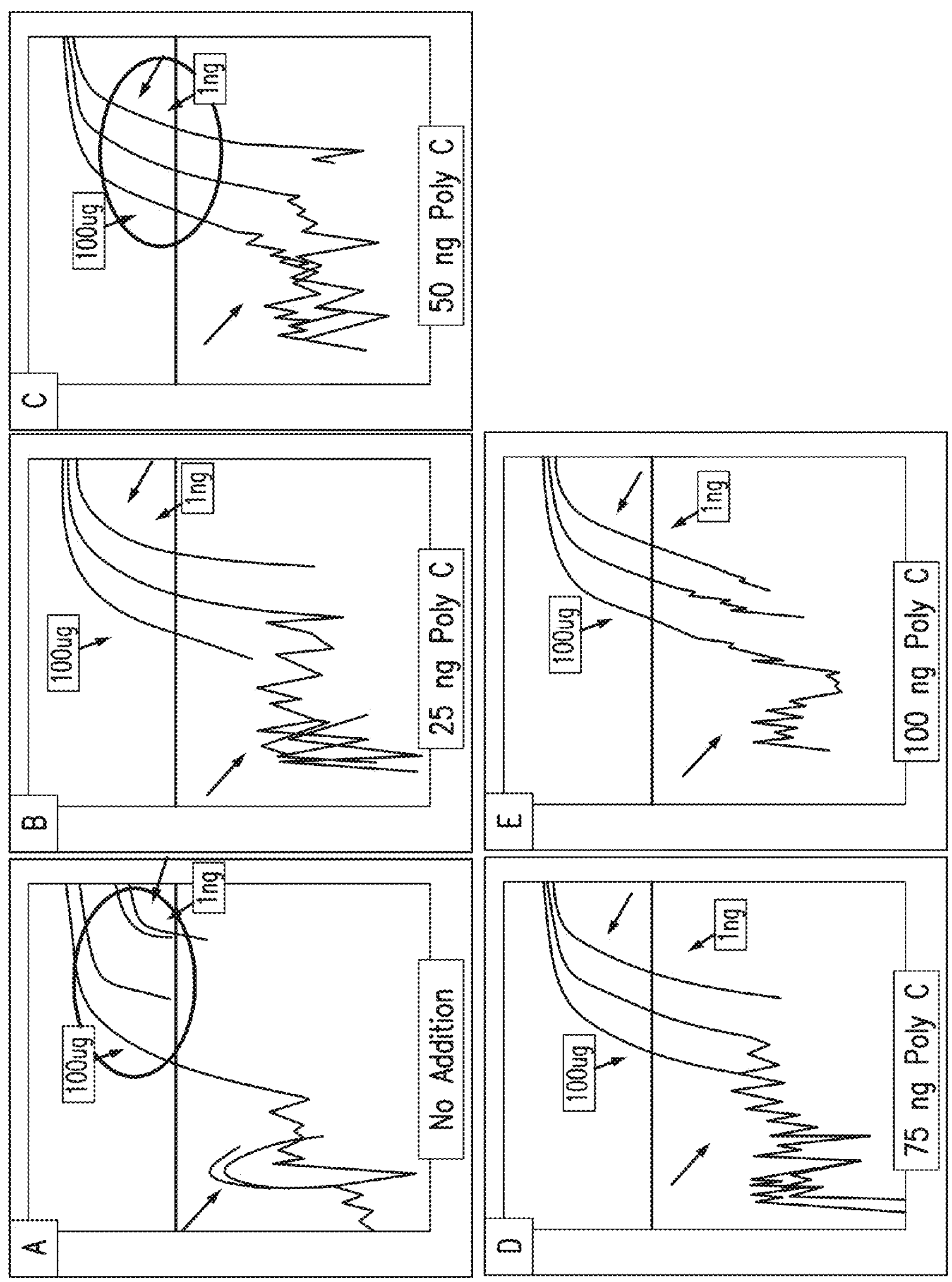

FIG. 22 shows various amounts (1-100 ng) of miRNeasy RNA, which were reverse transcribed with use of miScript in the presence or absence of various amounts of poly-(C). The thus produced cDNA was used in a real-time PCR, in this case to test CDC2.

Figure 23:
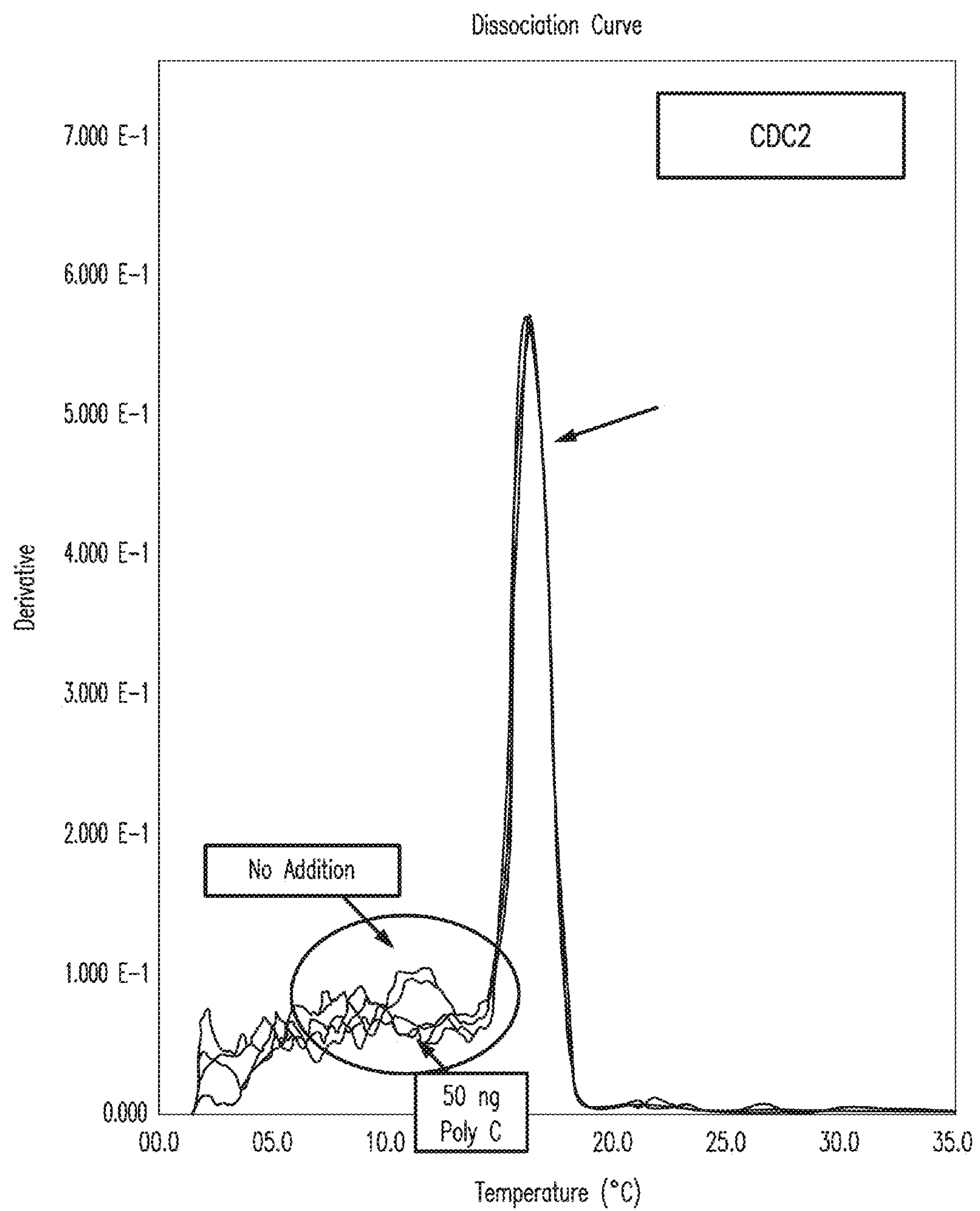

FIG. 23 shows the use of 1 ng of miRNeasy RNA, which was reverse transcribed in the presence or absence of 50 ng of poly-(C) and with use of the miScript RT Kit. The thus produced cDNA was tested in a real-time PCR to detect CDC2.

The invention claimed is:

1. A process for the synthesis of a cDNA, in an enzymatic reaction, wherein the process comprises:

(a) providing a reaction mixture comprising a ribonucleic acid, a first enzyme with polyadenylation activity, a second enzyme with reverse transcriptase activity, a buffer, at least one ribonucleotide, at least one deoxyribonucleotide, an anchor oligonucleotide, comprising a poly-(T)-oligonucleotide; and (b) incubating the reaction mixture in one or more temperature steps, which are selected such that the first enzyme and the second enzyme show activity, thereby forming said cDNA.

2. The process according to claim 1, wherein the ribonucleic acid is selected from the group that consisting of prokaryotic RNA, eukaryotic RNA, viral RNA, archae RNA, miRNA, snoRNA, mRNA, tRNA, non-polyadenylated RNA, rRNA and mixtures thereof.

3. The process according to claim 1, wherein the anchor oligonucleotide comprises a 5'-tail sequence.

4. The process according to claim 3, wherein the anchor oligonucleotide has a length of between 6 and 150 nucleotides, and optionally has an anchor sequence on the 3'-end.

5. The process according to claim 3, wherein the anchor oligonucleotide is a deoxyribonucleic acid (DNA), a peptide-nucleic acid (PNA), a locked nucleic acid (LNA), a phosphorus thioate-deoxyribonucleic acid, a cyclohexene-nucleic acid (CeNA), an N3'-P5'-phosphorus amidate (NP) or a tricyclo-deoxyribonucleic acid (tcDNA).

6. The process according to claim 1, wherein the ribonucleotide is selected from the group consisting of adenosine-5'-triphosphate, and a adenosine-5'-triphosphate with a base analog, wherein the ribonucleotide is optionally modified or labeled.

7. The process according to claim 1, wherein the deoxyribonucleotide is selected from the group that consisting of deoxyadenosine-5'triphosphate (dATP), deoxythymine-5'-triphosphate (dTTP), deoxycytosine-5'triphosphate (dCTP), deoxyguamine-5'-triphosphate (dGTP), deoxyuracil-5'-triphosphate (dUTP), and wherein the deoxyribonucleotide is optionally modified or labeled with a label.

8. The process according to claim 7, wherein the label is selected from the group consisting of a radioactive label, $^{32}P$, $^{33}P$, $^{35}S$, $^{3}H$, a fluorescent dye, fluorescein isothiocyanate (FITC), 6-carboxyfluorescein (FAM), xanthene, rhodamine, 6-carboxy-2',4',7',4,7-hexachlorofluorescein, 6-carboxy-4',5'-dichloro-2',7'-dimethoxy fluorescein, N,N,N',N'-tetramethyl-6-carboxyrhodamine, 6-carboxy-X-rhodamine, 5-carboxyrhodamine-6G, 6-carboxyrhodamine-6G, rhodamine 110;coumarins, umbelliferones, benzimides, phenanthridines, ethidium bromides, acridine dyes, carbazole dyes, phenoxazine dyes, porphyrine dyes, polymethine dyes; cyanine dyes, Cy3, Cy5, Cy7, quinoline dyes and alexa dyes.

9. The process according to claim 7, wherein the modification is selected from the group that comprises biotinylation, digoxigenin labeling and haptens.

10. The process according to claim 7, wherein the concentration of a deoxyribonucleotide is at least 0.01 mmol in the reaction and at most 10 mmol in the reaction.

11. The process according to claim 10, wherein the deoxyribonucleotides dATP, dCTP, dGTP and dTTP are present at a concentration of 0.2 mmol to 2 mmol.

12. The process according to claim 1, wherein the buffer has a pH of 6 to 10 and comprises $Mg^{2+}$ ions.

13. The process according to claim 1, wherein the enzyme with polyadenylation activity is selected from the group that consisting of enzymes of prokaryotic origin, eukaryotic origin, viral origin, archae origin and plant origin.

14. The process according to claim 13, wherein the enzyme with polyadenylation activity is selected from the group consisting of poly(A)-polymerase from *Escherichia coli*, poly (A)-polymerase from yeast, poly(A)-polymerase from cattle, poly(A)-polymerase from frogs, and human poly(A)-polymerase.

15. The process according to claim 1, wherein the enzyme with reverse transcriptase activity is selected from the group consisting of enzymes from viruses, bacteria, archae bacteria, eukaryotes and enzymes from thermostable organisms.

16. The process according to claim 15, wherein the enzyme with reverse transcriptase activity is selected from the group consisting of HIV Reverse Transcriptase, M-MLV Reverse Transcriptase, EAIV Reverse Transcriptase, AMV Reverse Transcriptase, *Thermus thermophilus* DNA polymerase I, M-MLV RNAse H.

17. The process according to claim 1, wherein the reaction additionally comprises a temperature step at a higher temperature of about 65° C. to 95° C.

18. The process according to claim 1, wherein the process further comprises amplifying said cDNA in a polymerase chain reaction using a random primer and/or specific primers and optionally one or more probes.

19. The process according to claim 1, wherein the reaction mixture further comprises a thermostable enzyme with DNA-synthesis activity, and at least one oligonucleotide for specific detection of cDNA.

20. The process according to claim 1, wherein the reaction comprises poly-(C)-polynucleotides.

* * * * *